United States Patent
Lee et al.

(10) Patent No.: US 11,130,734 B2
(45) Date of Patent: Sep. 28, 2021

(54) AMINO ALCOHOL-BORON-BINOL COMPLEX AND METHOD FOR PREPARING OPTICALLY ACTIVE AMINO ALCOHOL DERIVATIVE BY USING SAME

(71) Applicant: MOLECULES & MATERIALS CO., LTD., Daejeon (KR)

(72) Inventors: Kee In Lee, Daejeon (KR); Koteswara Rao Kamma, Andhrapradesh (IN); Venkata Subbaiah Sadu, Andhrapradesh (IN)

(73) Assignee: MOLECULES & MATERIALS CO., LTD., Daejeon (KR)

( * ) Notice: Subject to any disclaimer, the term of this patent is extended or adjusted under 35 U.S.C. 154(b) by 0 days.

(21) Appl. No.: 16/740,083

(22) Filed: Jan. 10, 2020

(65) Prior Publication Data
US 2021/0206719 A1    Jul. 8, 2021

(30) Foreign Application Priority Data

Jan. 6, 2020 (KR) ........................ 10-2020-0001522

(51) Int. Cl.
| | | |
|---|---|---|
| C07F 5/04 | (2006.01) | |
| C07D 213/30 | (2006.01) | |
| C07D 405/10 | (2006.01) | |
| C07D 239/26 | (2006.01) | |
| C07D 207/06 | (2006.01) | |
| C07D 333/20 | (2006.01) | |
| C07C 213/08 | (2006.01) | |
| C07D 295/092 | (2006.01) | |

(52) U.S. Cl.
CPC .......... *C07D 213/30* (2013.01); *C07C 213/08* (2013.01); *C07D 207/06* (2013.01); *C07D 239/26* (2013.01); *C07D 295/092* (2013.01); *C07D 333/20* (2013.01); *C07D 405/10* (2013.01); *C07F 5/04* (2013.01)

(58) Field of Classification Search
CPC ...................................................... C07F 5/04
See application file for complete search history.

(56) References Cited

U.S. PATENT DOCUMENTS

2008/0200672 A1    8/2008    Ortiz-marciales et al.

FOREIGN PATENT DOCUMENTS

| WO | 2008035358 A2 | 3/2008 |
| WO | 2008062473 A1 | 5/2008 |
| WO | 2008153289 A2 | 12/2008 |

OTHER PUBLICATIONS

Huang et al., "A Practical and Efficient Route for the Highly Enantioselective Synthesis of Mexiletine Analogues and Novel β-Thiophenoxy and Pyridyl Ethers", J. Org. Chem., 2008, 73, 6928-6931.
Huskens et al., "Direct Observation of Stereotopic Group Recognition in Solution and Solid State", J. Am. Chem. Soc., 1998, 120, 6617-6618.
Periasamy et al., "A Simple Convenient Method for the Resolution of Racemic 2,2'-Dihydroxy-1,1 '-Binaphthyl Using (S)-Proline", Tetrahedron: Asymmetry, 1995, vol. 6, No. 2, pp. 341-344.
Periasamy, "Syntheses of chiral amino alcohols and diols", Pure & Appl. Chem., 1996, vol. 68, No. 3, pp. 663-666.
Periasamy et al., "A New, Convenient Method of Resolution of Racemic 1,1'-Bi-2-naphthol Using Boric Acid and (R)-(+)-α-Methylbenzylamine" J. Org. Chem., 1999, 64, 7643-7645.
Bojadziev, et al., "Preparaion, Absolute Configuration and conformation of Some α-Aryl-2-pyridylmethanols", Bull. Chem. Soc. Jpn.,1987, 60, 2651-2655.
Zixing Shan et al., "Preparation and Properties of Chiral Spiroborate Esters with an O3BN Framework", Metal-Organic, and Nano-Metal Chemistry vol. 35:4 (2005): 275-279.
Sandeep Kumar Mishra et al., "In situ approach for testing the enantiopurity of chiral amines and amino alcohols by 1H NMR", Organic & Biomolecular Chemistry vol. 12,3 (2014): 495-502.
Sunita Goyal et al., "Synthesis and Spectroscopic Characterization of the First Mixed Six and Seven Membered Heterocyclic Boron Compounds With Intramolecular N—B Bond", Main Group Metal Chemistry vol. 32 (2009): 55-64.
Mariappan Periasamy et al., "New Methods of Resolution and Purification of Racemic and Diastereomeric Amino Alcohol Derivatives Using Boric Acid and Chiral 1,1'-Bi-2-naphthol", The Journal of Organic Chemistry vol. 66,11 (2001): 3828-33.
Yunbo Chu et al., "Asymmetric Reduction of Oxime Ethers Promoted by Chiral Spiroborate Esters with an O3BN Framework", The Journal of Organic Chemistry vol. 71,10 (2006): 3998-4001.

*Primary Examiner* — Brian E McDowell
(74) *Attorney, Agent, or Firm* — Rothwell, Figg, Ernst & Manbeck, P.C.

(57) ABSTRACT

Disclosed are an amino alcohol-boron-binol complex as an intermediate, including Complex 3-1-1 shown below, and a method for preparing an optically active amino alcohol by using the same, wherein a racemic amino alcohol is resolved in an enationselective manner using a boron compound and a (R)- or (S)-binol, whereby an amino alcohol derivative with high optical purity can be prepared at high yield.

3-1-1

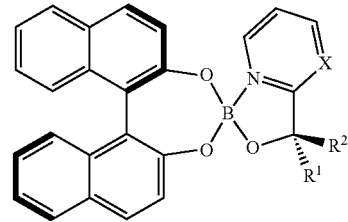

6 Claims, 1 Drawing Sheet

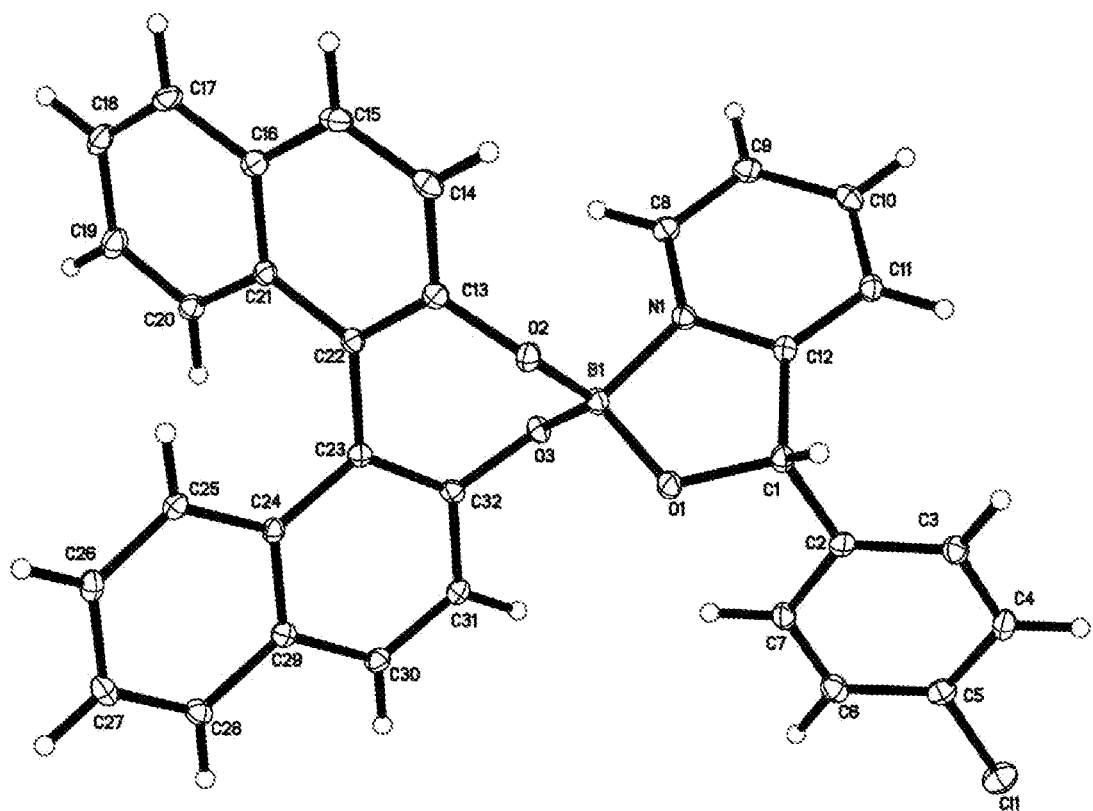

AMINO ALCOHOL-BORON-BINOL COMPLEX AND METHOD FOR PREPARING OPTICALLY ACTIVE AMINO ALCOHOL DERIVATIVE BY USING SAME

CROSS REFERENCE TO RELATED APPLICATION(S)

This application claims priority to Korean Application No. 10-2020-0001522, filed on Jan. 6, 2020, the entire disclosure of which is incorporated herein by reference.

BACKGROUND OF THE INVENTION

1. Field of the Invention

The present disclosure relates to an amino alcohol-boron-binol complex as an intermediate and a method for preparing an optically active amino alcohol derivative by using the same.

2. Description of the Related Art

Typical among chemically synthesized medication materials are racemates in which enantiomers are mixed. However, only one of the enantiomers in many racemic medications may be pharmacologically active whereas the other may be inactive or may even cause a side effect. For example, thalidomide exists in two mirror-image forms. Of the racemic mixture, one enantiomer has sedative effects whereas the other isomer is teratogenic. For ethambutol, one enantiomer is used to treat tuberculosis whereas another causes blindness. For naproxen, one enantiomer is used to treat arthritis pain whereas another causes liver poisoning with no analgesic effect. In addition, steroid receptors or penicillin show stereoselectivity. For the reason of exhibiting pharmacological effects without causing side effects, thus, the pharmaceutical industry requires the conversion of racemic materials to pharmaceutically effective single isomers or an approach of producing only single isomers in enantiopure forms in initial production steps.

Suggested as approaches for producing pure enantiomers are chiral resolution for the separation of racemic compounds into their enantiomers, and asymmetric synthesis for preparing chiral compounds from prochiral compounds.

Various natural products exist in nature. Natural products isolated from nature have complex structures and characteristic biological activities. The synthesis of natural products requires very effective asymmetric synthesis methods to the structural complexity and various stereochemical structures thereof. In order to effectively introduce stereochemical structures of molecules or biomolecules that have structural complexity, relatively simple natural products can be used as chiral building blocks or very frequent selection is made of natural products as a chiral pool for use in organic synthesis. Naturally occurring amino alcohols are versatile in morphology and biological activity and are themselves objects of organic synthesis methodology as well as being used as chiral auxiliaries or chiral ligands for organometallic catalyst.

The versatile structural characteristics of amino alcohols are very useful for the synthesis of natural products and biologically active materials and the development of novel drugs. Among others, medications with amino alcohol functional groups are found in as many as about 100 kinds of drugs including HIV protease inhibitors, β-blockers, selective serotonin reuptake inhibitors, oxazolidinone antibiotics, α/β-adrenergic agonists, NR1/2B subtype NMDA receptor antagonists, and so forth, indicating that an amino alcohol serves as a pharmacophore in various medications.

With respect to chiral resolution for preparation of amino alcohol derivatives, reference can be made to Stefan E. Bojadziev, et al., Bull. Chem. Soc. Jpn., 60(7), 2651-2655, 1987, which discloses the preparation of α-aryl-2-pyridyl methanol by chiral resolution using (−)-O,O'-dibenzoyl tartaric acid. However, the method requires four or more rounds of recrystallization due to the very low optical activity of the product and guarantees only a very low yield.

WO 2008/153289 discloses a method for preparation of bepostatine by chiral resolution of (RS)-4-[(4-chlorophenyl)(2-pyridyl)methoxy]piperidine.

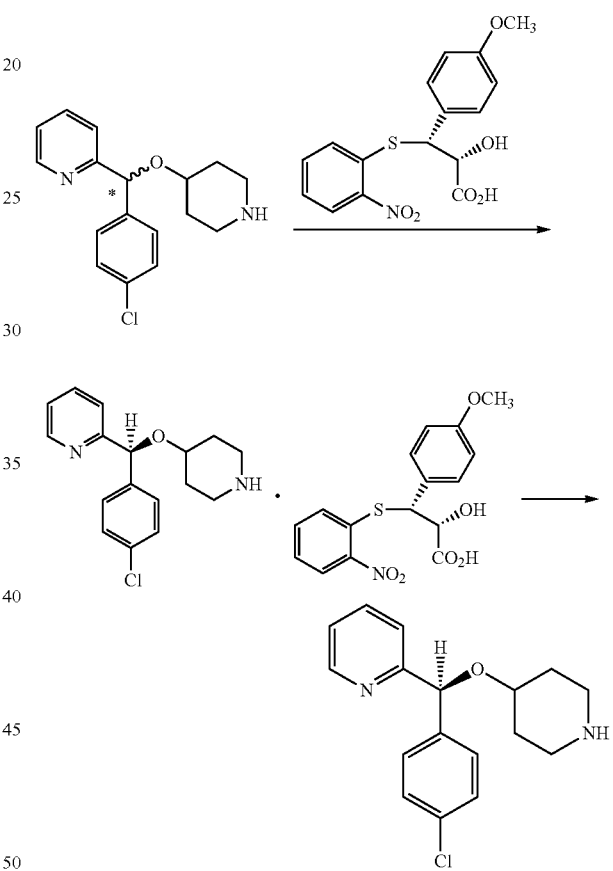

WO 2008/035358 A proposes a method for preparing dapoxetine by chiral solution for the amine group under the condition of protecting —OH with an organic substituent.

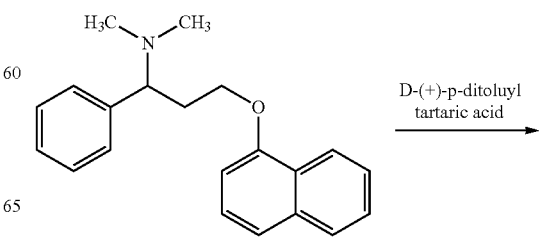

-continued

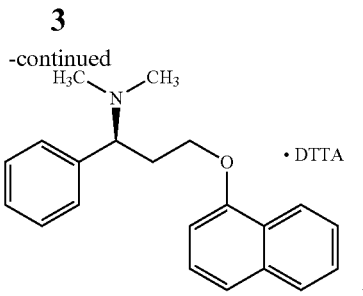

WO 2008/062473 A discloses a method for preparation of atomoxetine by chiral resolution for the amine group in the condition of protecting —OH group with an organic substituent. However, this disclosure is different from the present disclosure in which chiral resolution is possible in an initial step for the amino alcohol having an unsubstituted —OH group, with the resultant production of economic benefit, and various substitutions can be made on the —OH group, later.

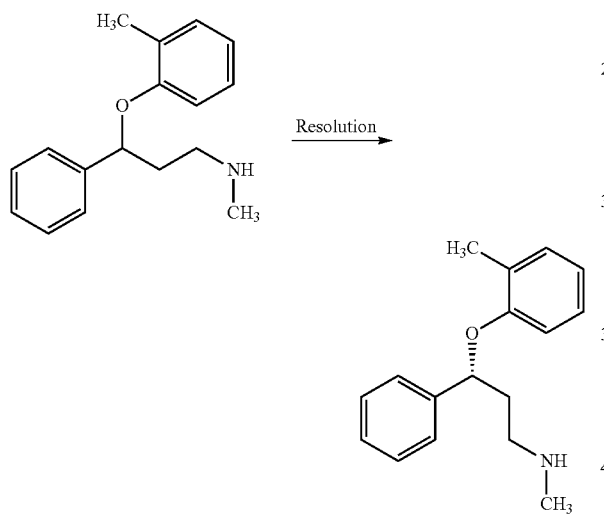

The synthesis of spiroborate ester is disclosed previously. For example, [Huskens, J. et al., J Am Chem Soc., 120(26), 6617-6618, 1998] introduces the reaction of amino alcohol, chiral diol, and triisopropyl borate at the rate of 1:1:1 for the synthesis of spiroborate ester. US. Patent No. 20080200672 A discloses the asymmetric reduction of ketone compounds, catalyzed by chiral spiroborate esters derived from chiral amino alcohols converted from amino acids. The asymmetric reduction of oxime ether compounds is disclosed in Huang, K. et al., J Org Chem., 73(17), 6928-6931, 2008).

Resolution of racemic binol by using spiroborate ester obtained from L-proline and racemic binol is reported in Periasamy M. et al., Pure & Appl. Chem., 68(3), 663-666, 1996, and Periasamy M. et al., Tetrahedron: Asymmetry, 6(2), 341-344, 1995. Obtained in this reaction, however, is a [Binol]$_2$[L-Proline] complex, but not a four-coordinate boron complex. As disclosed in Periasamy M. et al., J. Org. Chem., 64, 20, 7643-7645, 1999, resolution of racemic-amine with spiroborate ester leads to the production of a [(Binol)$_2$B][amine] complex, but not a 4-coordinate complex, either. However, there have not been reports on the formation of an amino alcohol-boron-binol complex (spiroborate ester) an intermediate for the synthesis of amino alcohol derivatives from a boron compound and binol ((R)- or (S)-binol) and the preparation of optically active amino alcohol derivatives therefrom, as in the present disclosure.

Intensive and thorough research into optically active amino alcohol derivatives, conducted by the present inventors, resulted in the finding that the use of an amino alcohol bearing a tertiary amine, a diol, and a boron compound at a specific ratio is very important for maximizing Peachey-Pope resolution. Peachey-Pope resolution uses ½ equivalents of a chiral resolving agent and ½ equivalents of an achiral agent as an auxiliary, instead of one equivalent of a chiral resolving agent. The achiral agent forms a diastereomeric salt or complex with a racemic amino alcohol, which dissolves well in the reaction solvent and thus is not easily crystalized, while a different diastereomeric salt or complex dissolves well in the reaction solvent and is crystallized with the concomitant assumption of most of the chiral resolving agent. Hence, the concentration of the chiral resolving agent in the reaction solution decreases with the progression of crystallization, whereas diastereomers remain dissolved in the reaction solution. This is illustrated in the following reaction scheme. For example, one equivalent of (1) is added with one equivalent of triisopropyl ester in acetonitrile to form one equivalent of (2), which dissolves well in the solvent. Reaction with about 0.5 equivalents of (3) affords the diastereomer (5), which is unlikely to dissolve in the solvent, but apt to crystallize. The crystallization proceeds with the concomitant consumption of most of (3) in the solution. After phase equilibrium, the diastereomer (4) remains dissolved in the solution wherein the diastereomer (5) with a high degree of crystallinity exists as a precipitate.

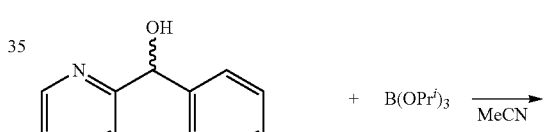

(1)

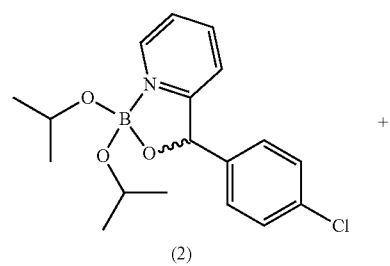

(2)

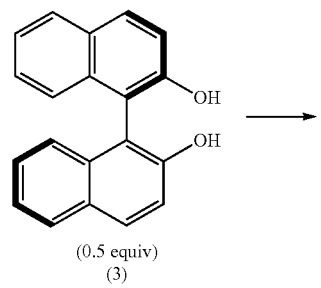

(0.5 equiv)
(3)

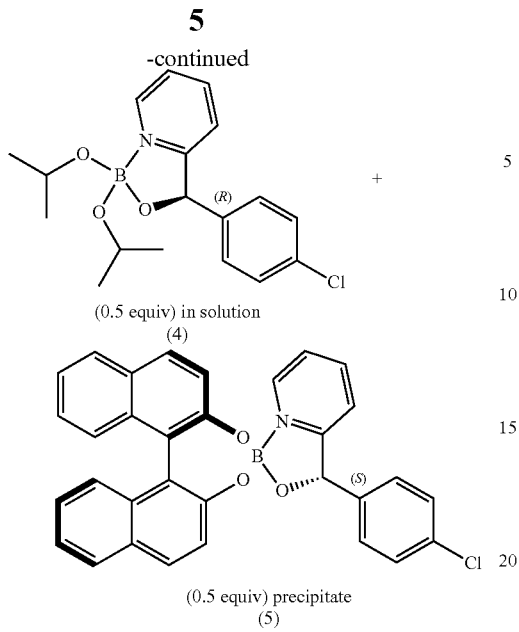

(0.5 equiv) in solution
(4)

+

(0.5 equiv) precipitate
(5)

As a result of the research, the present inventors discovered that an amino alcohol-boron-binol complex (spiroborate ester) can be easily obtained as an intermediate upon the reaction of controlled equivalents of the reactants and an optically active amino alcohol with high optical purify can be prepared at high yield by resolution with the aid of an amino alcohol-boron-binol complex (spiroborate ester), which led to the present disclosure.

SUMMARY OF THE INVENTION

A purpose of the present disclosure is to provide an amino alcohol-boron-binol complex as an intermediate for chiral resolution of a racemic amino alcohol and a method for preparing an optically active amino alcohol by using the same.

DESCRIPTION OF THE PREFERRED EMBODIMENTS

The present disclosure provides a method for preparing an optically active amino alcohol derivative from a racemic amino alcohol, the method comprising:
(first process) adding a racemic compound represented by the following Chemical Formula 1 with a boron compound, a (R)- or (S)-binol, and a solvent to form an amino alcohol-boron-binol complex as a precipitate; and
(second process) hydrolyzing the precipitate of the first process to acquire an optically active amino alcohol derivative:

[Chemical Formula 1]

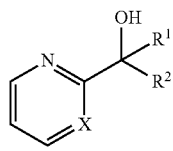

1-1

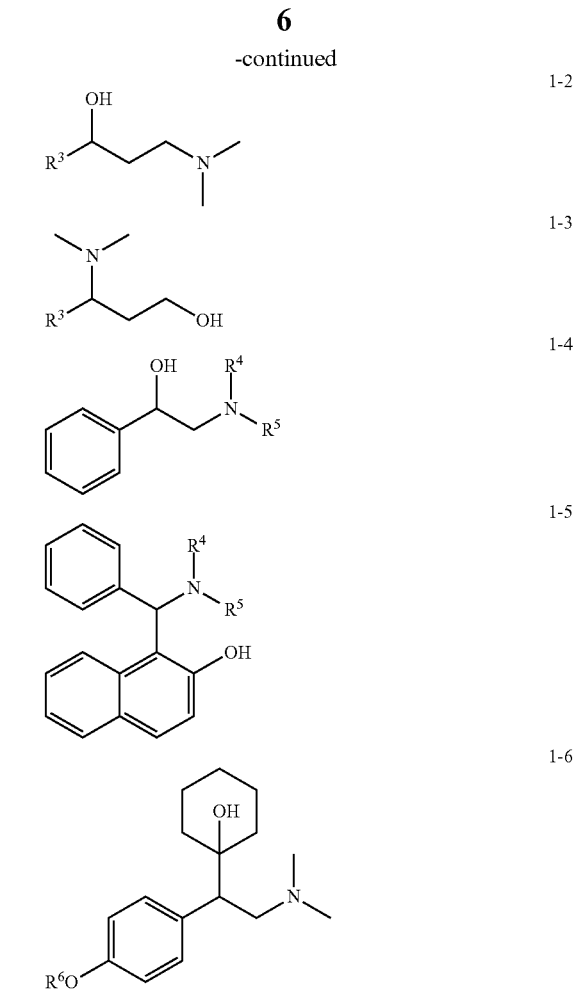

wherein,
X is CH, C—CH$_3$ or N;
R$^1$ is substituted with a hydrogen or a C$_1$-C$_{10}$ alkyl substituent;
R$^2$ is substituted with a substituent selected from the group consisting of a substituted or unsubstituted C$_1$-C$_{10}$ alkyl, a substituted or unsubstituted C$_2$-C$_{10}$ alkenyl, a substituted or unsubstituted C$_2$-C$_{10}$ alkynyl, a substituted or unsubstituted C$_4$-C$_{12}$ cycloalkyl, a substituted or unsubstituted C$_4$-C$_{12}$ heterocycloalkyl, a substituted or unsubstituted C$_4$-C$_{12}$ aryl, and a substituted or unsubstituted C$_4$-C$_{12}$ heteroaryl,
wherein the substituted alkyl, alkenyl, alkynyl, cycloalkyl, heterocycloalkyl, aryl, or heteroaryl has at least one substituent selected from the group consisting of hydrogen, halogen, hydroxy, amino, cyano, nitro, —S—(C$_1$-C$_{10}$ alkyl), C$_1$-C$_{10}$ haloalkyl, C$_1$-C$_{10}$ alkyl, and C$_1$-C$_{10}$ alkoxy;
R$^3$ is substituted with a substituted or unsubstituted C$_4$-C$_{12}$ aryl or a substituted or unsubstituted C$_4$-C$_{12}$ heteroaryl,
wherein the substituted aryl or heteroaryl has at least one substituent selected from the group consisting of hydrogen, halogen, hydroxy, amino, cyano, nitro, —S—(C$_1$-C$_{10}$ alkyl), C$_1$-C$_{10}$ haloalkyl, C$_1$-C$_{10}$ alkyl, and C$_1$-C$_{10}$ alkoxy;
R$^4$ and R$^5$ are each independently substituted with a substituent selected from the group consisting of a substituted or unsubstituted C$_1$-C$_{10}$ alkyl, a substituted or unsubstituted $C_4$-$C_{12}$ heterocycloalkyl, and a substituted or unsubstituted $C_4$-$C_{12}$ heteroaryl, wherein the substituted alkyl, heterocycloalkyl, or heteroaryl has at least one substituent selected from the group consisting of hydrogen, halogen, hydroxy, amino, cyano, nitro, —S—($C_1$-$C_{10}$ alkyl), $C_1$-$C_{10}$ haloalkyl, $C_1$-$C_{10}$ alkyl, and $C_1$-$C_{10}$ alkoxy; or $R^4$ and $R^5$ form together a substituted or unsubstituted $C_4$-$C_{12}$ heterocycloalkyl or a substituted or unsubstituted $C_4$-$C_{12}$ heteroaryl, wherein the substituted heterocycloalkyl or heteroaryl has at least one substituent selected from the group consisting of hydrogen, halogen, hydroxy, amino, cyano, nitro, —S—($C_1$-$C_{10}$ alkyl), $C_1$-$C_{10}$ haloalkyl, $C_1$-$C_{10}$ alkyl, and $C_1$-$C_{10}$ alkoxy; and $R^6$ is substituted with a substituent selected from the group consisting of hydrogen, a substituted or unsubstituted $C_1$-$C_{10}$ alkyl, and a substituted or unsubstituted $C_4$-$C_{12}$ aryl, wherein the substituted alkyl or aryl has at least one substituent selected from hydrogen, halogen, hydroxy, amino, cyano, nitro, —S—($C_1$-$C_{10}$ alkyl), $C_1$-$C_{10}$ haloalkyl, $C_1$-$C_{10}$ alkyl, and $C_1$-$C_{10}$ alkoxy.

The amino alcohol of the present disclosure is an amino alcohol bearing pyridine, pyrimidine, or a tertiary amine, wherein the alcohol moiety may be a primary, secondary, or tertiary alcohol. In addition, the amino alcohol has the chemical structure of 1,2-amino alcohol or 1,3-amino alcohol in which the tertiary amine and the primary, secondary, or tertiary alcohol can form a 5- or 6-membered complex with the boron compound.

In the first process, the boron compound is particularly selected from the group consisting of boric acid, trimethyl borate, triethyl borate, triisopropyl borate, tributyl borate, triphenyl borate, and a combination thereof, but is not limited thereto.

In the first process, (R)- or (S)-binol is selected from the chemical structures represented by the following Chemical Formula 2, but is not limited thereto. A substituted or unsubstituted (R)- or (S)-binol may be used.

[Chemical Formula 2]

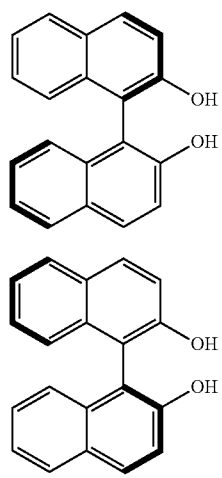

2-1

2-2

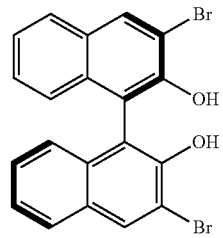

2-3

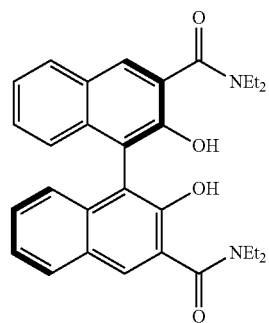

2-4

The solvent in the first process may be selected from the group consisting of acetonitrile, dichloromethane, toluene, isopropanol, and a combination thereof, but any organic solvent may be available without particular limitations thereto.

For a stoichiometric reaction in the first process, the boron compound and the (R)- or (S)-binol are used in amounts of 1 mole equivalent and 0.45-0.6 mole equivalents, respectively, based on 1 mole equivalent of the racemic compound represented by Chemical Formula 1. Given an amount beyond the stoichiometric range, the reaction is conducted insufficiently or produces a byproduct, with the resultant decrease of the optical purify and yield. Hence, the reaction with the stoichiometric amounts is particularly important.

In the second process, the hydrolysis of the precipitate may be achieved with an acid or a base and particularly with oxalic acid, acetic acid, hydrochloric acid, sulfuric acid, nitric acid, sodium hydroxide, lithium hydroxide, or potassium hydroxide, but with no limitations thereto.

After the reaction is terminated in the method of the present disclosure, the optically active amino alcohol derivative may be purified using a typical isolation or purification method such as chromatography, but without limitations thereto.

In addition, the present disclosure relates to an amino alcohol-boron-binol complex (spiroborate ester) represented by the following Chemical Formula 3:

[Chemical Formula 3]

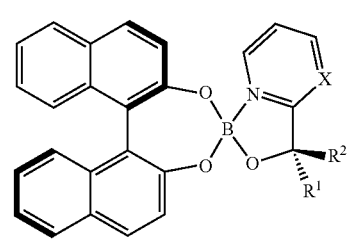

3-1-1

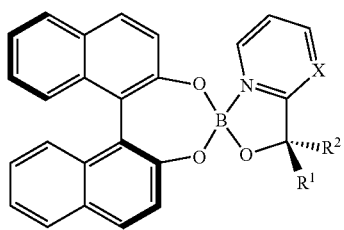

3-1-2

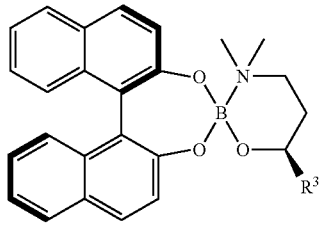

3-2-1

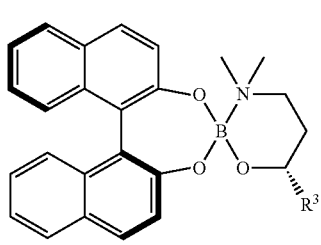

3-2-2

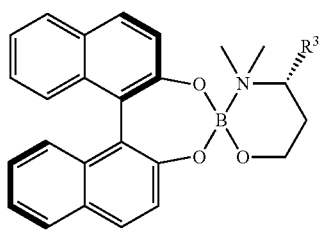

3-3-1

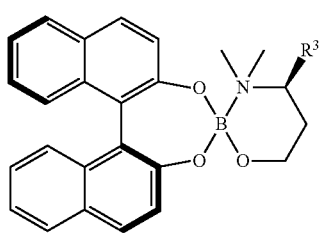

3-3-2

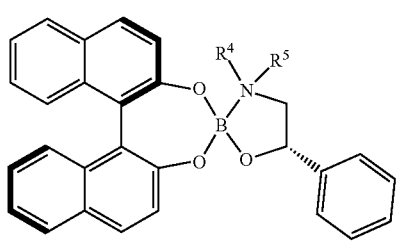

3-4-1

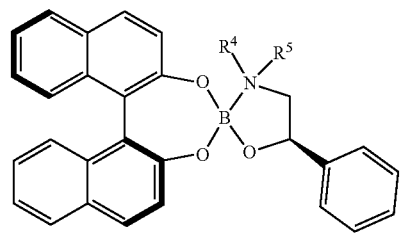

3-4-2

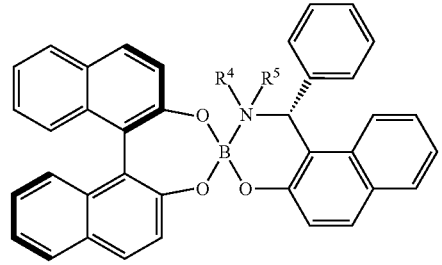

3-5-1

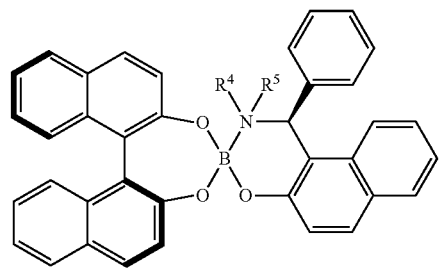

3-5-2

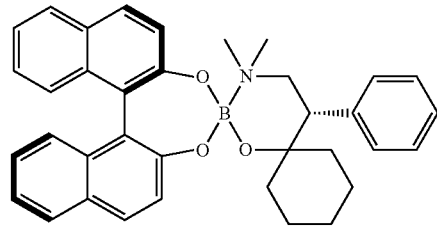

3-6-1

3-6-2 wherein,
X is CH, C—CH$_3$ or N;
R$^1$ is substituted with a hydrogen or a C$_1$-C$_{10}$ alkyl substituent;
R$^2$ is substituted with a substituent selected from the group consisting of a substituted or unsubstituted C$_1$-C$_{10}$ alkyl, a substituted or unsubstituted C$_2$-C$_{10}$ alkenyl, a substituted or unsubstituted C$_2$-C$_{10}$ alkynyl, a substituted or unsubstituted C$_4$-C$_{12}$ cycloalkyl, a substituted or unsubstituted C$_4$-C$_{12}$ heterocycloalkyl, a substituted or unsubstituted C$_4$-C$_{12}$ aryl, and a substituted or unsubstituted C$_4$-C$_{12}$ heteroaryl,
wherein the substituted alkyl, alkenyl, alkynyl, cycloalkyl, heterocycloalkyl, aryl, or heteroaryl has at least one substituent selected from the group consisting of hydrogen, halogen, hydroxy, amino, cyano, nitro, —S—($C_1$-$C_{10}$ alkyl), $C_1$-$C_{10}$ haloalkyl, $C_1$-$C_{10}$ alkyl, and $C_1$-$C_{10}$ alkoxy;

$R^3$ is substituted with a substituted or unsubstituted $C_4$-$C_{12}$ aryl or a substituted or unsubstituted $C_4$-$C_{12}$ heteroaryl, wherein the substituted aryl or heteroaryl has at least one substituent selected from the group consisting of hydrogen, halogen, hydroxy, amino, cyano, nitro, —S—($C_1$-$C_{10}$ alkyl), $C_1$-$C_{10}$ haloalkyl, $C_1$-$C_{10}$ alkyl, and $C_1$-$C_{10}$ alkoxy;

$R^4$ and $R^5$ are each independently substituted with a substituent selected from the group consisting of a substituted or unsubstituted $C_1$-$C_{10}$ alkyl, a substituted or unsubstituted $C_4$-$C_{12}$ heterocycloalkyl, and a substituted or unsubstituted $C_4$-$C_{12}$ heteroaryl, wherein the substituted alkyl, heterocycloalkyl, or heteroaryl has at least one substituent selected from the group consisting of hydrogen, halogen, hydroxy, amino, cyano, nitro, —S—($C_1$-$C_{10}$ alkyl), $C_1$-$C_{10}$ haloalkyl, $C_1$-$C_{10}$ alkyl, and $C_1$-$C_{10}$ alkoxy; or $R^4$ and $R^5$ form together a substituted or unsubstituted $C_4$-$C_{12}$ heterocycloalkyl or a substituted or unsubstituted $C_4$-$C_{12}$ heteroaryl, wherein the substituted heterocycloalkyl or heteroaryl has at least one substituent selected from the group consisting of hydrogen, halogen, hydroxy, amino, cyano, nitro, —S—($C_1$-$C_{10}$ alkyl), $C_1$-$C_{10}$ haloalkyl, $C_1$-$C_{10}$ alkyl, and $C_1$-$C_{10}$ alkoxy; and $R^6$ is substituted with a substituent selected from the group consisting of hydrogen, a substituted or unsubstituted $C_1$-$C_{10}$ alkyl, and a substituted or unsubstituted $C_4$-$C_{12}$ aryl, wherein the substituted alkyl or aryl has at least one substituent selected from hydrogen, halogen, hydroxy, amino, cyano, nitro, —S—($C_1$-$C_{10}$ alkyl), $C_1$-$C_{10}$ haloalkyl, $C_1$-$C_{10}$ alkyl, and $C_1$-$C_{10}$ alkoxy.

The following terms have the following meanings unless otherwise indicated. Any undefined terms have their art recognized meanings.

The term "halogen" refers to fluorine (F), chlorine (Cl), bromine (Br), or iodine (I).

The term "alkyl" refers to a monovalent, linear, or branched hydrocarbon radical. The term includes, by way of example, methyl, ethyl, propyl, n-butyl, isobutyl, tert-butyl, and 1-methylpropyl.

The term "alkenyl" or "alkynyl" refers to a linear or branched hydrocarbon radical bearing one or more double or triple bonds.

The term "alkoxy" refers to an oxygen bonded to a monovalent, linear or branched, saturated hydrocarbon. Alkoxy includes, by way of example, methoxy, ethoxy, propoxy, n-butoxy, tert-butoxy, and 1-methylpropoxy.

The term "cycloalkyl" refers to a monovalent monocyclic saturated hydrocarbon. Cycloalkyl includes, by way of example, cyclopropyl, cyclobutyl, cyclopentyl, cyclohexyl, cycloheptyl, and cyclooctyl.

The term "aryl" refers to an aromatic substituent having at least one ring with a p-system of electrons delocalized therein, as exemplified by phenyl, benzyl, etc.

The term "heteroaryl" refers to an aromatic ring compound bearing a heteroatom such as N, O, or S as a ring member. Examples of heteroaryl include pyrrolyl, furanyl, pyridinyl, pyrimidinyl, and pyranyl, according to numbers and kinds of the heteroatoms and numbers of carbon atoms within the ring.

The term "enantiomeric excess (ee)" refers to a parameter of optical purity used for enantiomers in racemic mixtures, reflecting a difference in mole fraction between individual enantiomers in a racemate. A sample with 80 moles of (R)-enantiomer and 20 moles of (S)-enantiomer has an enantiomeric excess (ee) of 180−201=60% for the (R)-enantiomer. Accordingly, an ee of 80% or greater means that the amount of a desired enantiomer accounts for 90% or greater of a racemic mixture.

The present disclosure pertains to an amino alcohol-boron-binol complex as an intermediate and a method for preparation of an optically active amino alcohol by using the same, in which the optical active amino alcohol with a high optical purity can be prepared at high yield from a racemic amino alcohol by chiral resolution using a boron compound and a (R)- or (S)-binol.

A better understanding of the present invention may be obtained through the following examples which are set forth to illustrate, but are not to be construed as limiting the present invention.

Example 1: Preparation and Physicochemical Characterization of Optically Active Amino Alcohol Derivative 1. Preparation of Compound 1: (S)-(4-chlorophenyl)(pyridine-2-yl)methanol

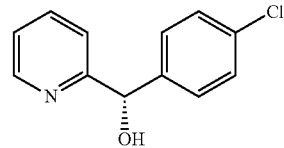 [SMILES: O[C@@H](c1ccc(Cl)cc1)c1ccccn1]

(Step 1) To a solution of racemic (4-chlorophenyl) (pyridine-2-yl)methanol (219.7 mg, 1.0 mmol) in acetonitrile (6 ml) was added B(OiPr)$_3$ (188 mg, 1.0 mmol) at room temperature, followed by (R)-binol (128 mg, 0.45 mmol). After stirring at room temperature for 72 hours, the precipitate thus formed was filtered, washed with acetonitrile (1 ml), and then dried to afford an amino alcohol-boron-binol complex (spiroborate complex, 200 mg, yield 38.9%) as a white solid. The HRMS data were as follows:

HRMS (EI) calculated for $C_{32}H_{21}$ BNO$_3$Cl [M+H]$^+$: 513.1303, found: 513.1303.

The following structure was constructed as analyzed by X-ray diffraction patterns. In detail, the structure accounts for (S)-(4-chlorophenyl)(pyridine-2-yl)methanol-boron-binol complex in which the central atom B is connected to (R)-binol via two B—O bonds and to the substrate via one B—O bond and a B—N coordinate bond.

(Step 2) The spiroborate complex (200 mg, 0.389 mmol) was fractioned between ethyl acetate (30 ml) and 2N HCl (20 ml) and stirred at room temperature for 1 hour. The aqueous layer thus separated was washed with ethyl acetate (10 ml) and the pH was adjusted to 7 with saturated sodium hydrogen carbonate, followed by extraction with dichloromethane (2×20 ml). The extracted organic layers were pooled, dried over anhydrous sodium sulfate, and concentrated to afford Compound 1 (84 mg, 0.38 mmol, 98% ee). Physicochemical data of Compound 1 are given as follows:

$^1$H NMR (400 MHz, CDCl$_3$) δ 8.57-8.51 (m, 1H), 7.69-7.59 (m, 1H), 7.40-7.26 (m, 4H), 7.24-7.13 (m, 2H), 5.74 (d, J=1.5 Hz, 1H), 5.64-5.33 (m, 1H);

$^{13}$C NMR (100 MHz, CDCl$_3$) δ 160.65, 160.63, 148.00, 141.79, 137.03, 133.56, 128.71, 128.41, 122.64, 121.23, 74.43;

HPLC: Chiralpack AD-H column, hexanes:isopropanol=95:5, UV detection at 220 nm, Flow rate 1.0 ml/min, tR (minor isomer)=21.4 min, tR (major isomer)=27.6 min, 98% ee;

[α]$_D$=+90.5 (c 0.5, EtOH).

In the present disclosure, when 0.45 equivalents of a solution of (R)-binol is added to a solution of 1 equivalent of triisopropyl borate in 1 equivalent of racemic-(4-chlorophenyl)(pyridine-2-yl)methanol, precipitation starts to form a white crystal and is completed within 72 hours. The resulting precipitate retains a very high degree of crystallinity and thus is unlikely to dissolve in most NMR solvents, but tends to dissolve in protic or polar solvents. However, molecular ions of the precipitate can be detected using mass spectroscopy. In addition, X-ray crystallography identified the precipitate as a 4-coordinate boron complex having (S)-(4-chlorophenyl)(pyridine-2-yl)methanol. This 4-coordinate boron complex was hydrolyzed in a conventional manner to obtain Compound 1 ((S)-(4-chlorophenyl)(pyridine-2-yl)methanol) with high optical purity.

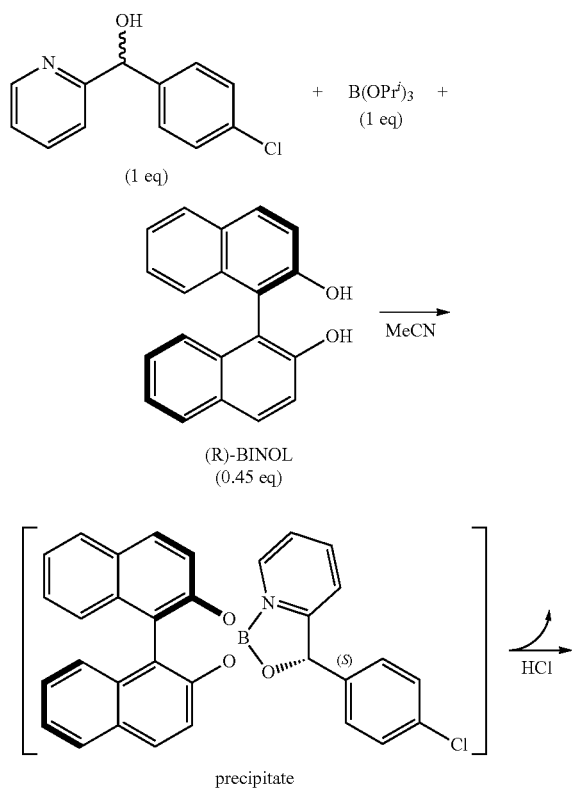

2. Preparation of Compound 2:
(R)-(4-chlorophenyl)(pyridine-2-yl)methanol

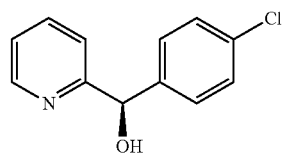 [SMILES: O[C@H](c1ccc(Cl)cc1)c1ccccn1]

The same procedure as for Compound 1 was conducted, with the exception of using 0.45 equivalents of (S)-binol instead of (R)-binol (128 mg, 0.45 mmol), to prepare Compound 2 (40% yield, 97% ee).

[α]$_D$=−90.1 (c 0.21, EtOH).

3. Preparation of Compound 3:
(S)-(4-methoxyphenyl)(pyridine-2-yl)methanol

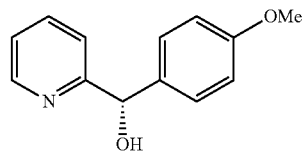 [SMILES: COc1ccc([C@H](O)c2ccccn2)cc1]

The same procedure as for Compound 1 was conducted, with the exception of using racemic (4-methoxyphenyl)(pyridine-2-yl)methanol (215 mg, 1.0 mmol) instead of racemic (4-chlorophenyl)(pyridine-2-yl)methanol (219.7 mg, 1.0 mmol), to prepare Compound 3 (80 mg, 0.37 mmol, 95% ee). HRMS data for the amino alcohol-boron-binol complex are given, together with physicochemical properties thereof, as follows:

HRMS (EI) calculated for C$_{33}$H$_{24}$BNO$_4$ [M]$^+$: 507.1798, found: 507.1801;

$^1$H NMR (500 MHz, CDCl$_3$) 8.58-8.53 (m, 1H), 7.66-7.59 (m, 1H), 7.33-7.27 (m, 2H), 7.23-7.15 (m, 2H), 6.92-6.85 (m, 2H), 5.74 (s, 1H), 5.30 (s, 1H), 3.80 (s, 3H);

$^{13}$C NMR (126 MHz, CDCl$_3$) 161.32, 159.25, 147.81, 136.84, 135.50, 128.37, 122.35, 121.30, 113.98, 74.63, 55.27;

HPLC: Chiralpack AD-H column, hexanes:isopropanol=95:5, UV detection at 220 nm, Flow rate 0.8 ml/min, tR (minor isomer)=22.31 min, tR (major isomer)=25.80 min, 95% ee;

[α]$_D$=+21.6 (c 0.5, EtOH).

4. Preparation of Compound 4:
(S)-(3-methylpyridine-2-yl)(phenyl)methanol

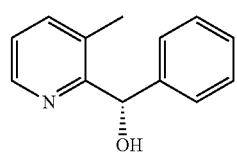

The same procedure as for Compound 1 was conducted, with the exception of using racemic (3-methylpyridine-2-yl)(phenyl)methanol (200 mg, 1.0 mmol) instead of racemic (4-chlorophenyl)(pyridine-2-yl)methanol (219.7 mg, 1.0 mmol), to prepare Compound 4 (78 mg, 0.39 mmol, 81% ee). HRMS data for the amino alcohol-boron-binol complex are given, together with physicochemical properties of Compound 4, as follows:

HRMS (EI) calculated for $C_{33}H_{24}BNO_3$ [M]$^+$: 493.1849, found: 493.1854;

$^1$H NMR (500 MHz, CDCl$_3$) 8.53-8.39 (m, 1H), 7.49-7.43 (m, 1H), 7.36-7.24 (m, 5H), 7.24-7.18 (m, 1H), 6.29-5.86 (m, 1H), 5.77 (s, 1H), 2.11 (s, 3H);

$^{13}$C NMR (126 MHz, CDCl$_3$) 157.82, 144.88, 142.24, 138.55, 130.37, 128.47, 127.75, 127.67, 122.65, 72.48, 17.82.

HPLC: Chiralpack AD-H column, hexanes:isopropanol=95:5, UV detection at 220 nm, Flow rate 1.0 ml/min, tR (major isomer)=11.23 min, tR (minor isomer), 81% ee;

$[\alpha]_D$=−24.6 (c 0.5, EtOH).

5. Preparation of Compound 5: (S)-benzo[d][1,3]dioxol-5-yl(pyridine-2-yl)methanol

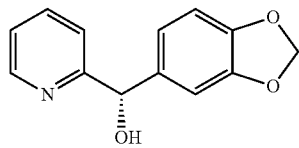 [SMILES: O[C@@H](c1ccc2c(c1)OCO2)c1ccccn1]

The same procedure as for Compound 1 was conducted, with the exception of using racemic benzo[d][1,3]dioxol-5-yl(pyridine-2-yl)methanol (230 mg, 1.0 mmol) instead of racemic (4-chlorophenyl)(pyridine-2-yl)methanol (219.7 mg, 1.0 mmol), to prepare Compound 5 (86 mg, 0.37 mmol, 96% ee). HRMS data for the amino alcohol-boron-binol complex are given, together with physicochemical properties of Compound 5, as follows:

HRMS (EI) calculated for $C_{33}H_{22}BNO_5$ [M]$^+$: 523.1591, found: 523.1590;

$^1$H NMR (500 MHz, CDCl$_3$) 8.59-8.54 (m, 1H), 7.67-7.60 (m, 1H), 7.24-7.15 (m, 2H), 6.92-6.87 (m, 1H), 6.84-6.76 (m, 2H), 5.95 5.91 (m, 2H), 5.68 (s, 1H);

$^{13}$C NMR (126 MHz, CDCl$_3$) 160.96, 147.92, 147.80, 147.25, 137.34, 136.88, 122.44, 121.28, 120.76, 108.10, 107.43, 101.04, 74.76.

HPLC: Chiralpack AD-H column, hexanes:isopropanol=90:10, UV detection at 220 nm, Flow rate 0.8 ml/min, tR (minor isomer)=27.32 min, tR (major isomer)=30.80 min, 96% ee;

$[\alpha]_D$=−3.8 (c 0.5, CHCl$_3$).

6. Preparation of Compound 6: (S)-phenyl(pyridine-2-yl)methanol

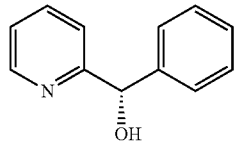 [SMILES: O[C@@H](c1ccccc1)c1ccccn1]

The same procedure as for Compound 1 was conducted, with the exception of using racemic phenyl(pyridine-2-yl)methanol (186 mg, 1.0 mmol) instead of racemic (4-chlorophenyl)(pyridine-2-yl)methanol (219.7 mg, 1.0 mmol), to prepare Compound 6 (70 mg, 0.38 mmol, 62% ee). HRMS data for the amino alcohol-boron-binol complex are given, together with physicochemical properties of Compound 6, as follows:

HRMS (EI) calculated for $C_{32}H_{22}BNO_3$ [M]$^+$: 479.1693, found: 479.1693;

$^1$H NMR (400 MHz, CDCl$_3$) 8.61-8.55 (m, 1H), 7.69-7.60 (m, 1H), 7.47-7.33 (m, 4H), 7.33-7.27 (m, 1H), 7.25-7.15 (m, 2H), 5.79 (d, J=1.9 Hz, 1H), 5.38 (s, 1H);

$^{13}$C NMR (100 MHz, CDCl$_3$) 160.96, 160.94, 147.86, 143.26, 136.87, 128.60, 127.84, 127.09, 122.45, 121.37, 77.41, 77.09, 76.77, 75.03;

HPLC: Chiralpack AD-H column, hexanes:isopropanol=95:5, UV detection at 220 nm, Flow rate 1.0 ml/min, tR (minor isomer)=23.7 min, tR (major isomer)=28.7 min, 62% ee;

$[\alpha]_D$=+20.5 (c 0.5, EtOH).

6-1. Preparation of Compound 6: (S)-phenyl(pyridine-2-yl)methanol

The same procedure as for Compound 6 was conducted, with the exception of using 0.45 equivalents of (R)-3,3'-(CONEt$_2$)$_2$-binol instead of (R)-binol (128 mg, 0.45 mmol), to prepare Compound 6 at a yield 35% and an ee of 98%.

$[\alpha]_D$=+28.9 (c 0.5, EtOH).

7. Preparation of Compound 7: (S)-(4-fluorophenyl)(pyridine-2-yl)methanol

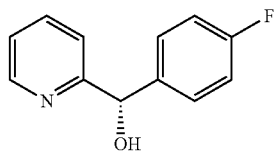 [SMILES: O[C@@H](c1ccc(F)cc1)c1ccccn1]

The same procedure as for Compound 1 was conducted, with the exception of using racemic (4-fluorophenyl)(pyridine-2-yl)methanol (204 mg, 1.0 mmol) instead of racemic (4-chlorophenyl)(pyridine-2-yl)methanol (219.7 mg, 1.0 mmol), to prepare Compound 7 (76 mg, 0.37 mmol, 73% ee). HRMS data for the amino alcohol-boron-binol complex are given, together with physicochemical properties of Compound 7, as follows:

HRMS (EI) calculated for $C_{32}H_{21}BFNO_3$ [M]$^+$: 497.1599 found: 497.1599;

$^1$H NMR (400 MHz, CDCl$_3$) 8.58-8.52 (m, 1H), 7.71-7.59 (m, 1H), 7.42-7.31 (m, 2H), 7.25-7.13 (m, 2H), 7.07-6.97 (m, 2H), 5.76 (s, 1H), 5.48 (s, 1H);

$^{13}$C NMR (100 MHz, CDCl$_3$) 163.60, 161.16, 160.92, 160.89, 147.94, 139.12, 139.09, 136.97, 128.80, 128.72, 122.55, 121.24, 115.51, 115.29, 74.41;

HPLC: Chiralpack AD-H column, hexanes:isopropanol=95:5, UV detection at 220 nm, Flow rate 1.0 ml/min, tR (minor isomer)=13.0 min, tR (major isomer)=15.36 min, 73% ee;

$[\alpha]_D$=+60.0 (c 0.5, EtOH).

8. Preparation of Compound 8:
(S)-pyridin-2-yl(o-tolyl)methanol

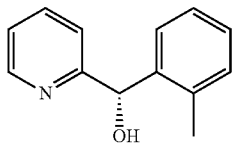

The same procedure as for Compound 1 was conducted, with the exception of using racemic pyridine-2-yl(o-tolyl)methanol (200 mg, 1.0 mmol) instead of racemic (4-chlorophenyl)(pyridine-2-yl)methanol (219.7 mg, 1.0 mmol), to prepare Compound 8 (82 mg, 0.38 mmol, 57% ee). HRMS data for the amino alcohol-boron-binol complex are given, together with physicochemical properties of Compound 8, as follows:

HRMS (EI) calculated for $C_{33}H_{24}BNO_3$ [M]$^+$: 493.1849, found: 493.1847;

$^1$H NMR (500 MHz, CDCl$_3$) 8.67-8.53 (m, 1H), 7.70-7.57 (m, 1H), 7.31-7.25 (m, 1H), 7.25-7.17 (m, 4H), 7.09-7.03 (m, 1H), 6.00 (s, 1H), 2.36 (s, 3H);

$^{13}$C NMR (126 MHz, CDCl$_3$) 160.89, 147.75, 140.59, 136.81, 136.20, 130.78, 127.97, 127.77, 126.10, 122.27, 121.18, 77.26, 77.01, 76.75, 72.75, 19.41;

HPLC: Chiralpack AD-H column, hexanes:isopropanol=95:5, UV detection at 220 nm, Flow rate 1.0 ml/min, tR (minor isomer)=18.2 min, tR (major isomer)=22.48 min, 57% ee.

$[\alpha]_D$=+10.2 (c 0.5, EtOH).

8-1. Preparation of Compound 8:
(S)-pyridine-2-yl(o-tolyl)methanol

The same procedure as for Compound 8 was conducted, with the exception of using 0.45 equivalents of (R)-3,3'-(CONEt$_2$)$_2$-binol instead of (R)-binol (128 mg, 0.45 mmol), to prepare Compound 8 at a yield of 35% and an ee of 86%.

$[\alpha]_D$=+32.3 (c 0.5, EtOH).

9. Preparation of Compound 9:
(S)-(4-methylphenyl)(pyridine-2-yl)methanol

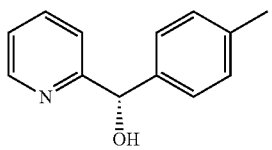

The same procedure as for Compound 1 was conducted, with the exception of using racemic (4-methylphenyl)(pyridine-2-yl)methanol (200 mg, 1.0 mmol) instead of racemic (4-chlorophenyl)(pyridine-2-yl)methanol (219.7 mg, 1.0 mmol), to prepare Compound 9 (80 mg, 0.40 mmol, 79% ee). HRMS data for the amino alcohol-boron-binol complex are given, together with physicochemical properties of Compound 9, as follows:

HRMS (EI) calculated for $C_{33}H_{24}BNO_3$ [M]$^+$: 493.1849, found: 493.1851;

$^1$H NMR (500 MHz, CDCl$_3$) 8.61-8.57 (m, 1H), 7.67-7.60 (m, 1H), 7.29 (d, J=8.1 Hz, 3H), 7.25-7.15 (m, 4H), 5.75 (d, J=4.0 Hz, 1H), 5.24 (d, J=4.3 Hz, 1H), 2.35 (s, 3H);

$^{13}$C NMR (126 MHz, CDCl$_3$) 161.22, 147.83, 140.36, 137.51, 136.84, 129.27, 127.02, 122.36, 121.33, 74.88, 21.17;

HPLC: Chiralpack AD-H column, hexanes:isopropanol=90:10, UV detection at 220 nm, Flow rate 0.8 ml/min, tR (minor isomer)=12.62 min, tR (major isomer)=14.35 min, 79% ee;

$[\alpha]_D$=+24.2 (c 0.5, EtOH).

10. Preparation of Compound 10:
(S)-(3-methylphenyl)(pyridine-2-yl)methanol

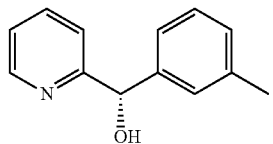

The same procedure as for Compound 1 was conducted, with the exception of using racemic (3-methylphenyl)(pyridine-2-yl)methanol (200 mg, 1.0 mmol) instead of racemic (4-chlorophenyl)(pyridine-2-yl)methanol (219.7 mg, 1.0 mmol), to prepare Compound 10 (72 mg, 0.36 mmol, 89% ee). HRMS data for the amino alcohol-boron-binol complex are given, together with physicochemical properties of Compound 10, as follows:

HRMS (EI) calculated for $C_{33}H_{24}BNO_3$ [M]$^+$: 493.1849, found: 493.1843;

$^1$H NMR (500 MHz, CDCl$_3$) 8.55 (s, 1H), 7.65-7.60 (m, 1H), 7.25-7.16 (m, 5H), 7.10 (d, J=7.5 Hz, 1H), 5.73 (s, 1H), 5.26 (br s, 1H), 2.33 (s, 3H);

$^{13}$C NMR (126 MHz, CDCl$_3$) 161.22, 147.83, 143.15, 138.32, 136.84, 128.63, 128.53, 127.71, 124.23, 122.42, 121.43 75.0, 21.54;

HPLC: Chiralpack AD-H column, hexanes:isopropanol=90:10, UV detection at 220 nm, Flow rate 0.8 ml/min, tR (minor isomer)=12.62 min, tR (major isomer)=14.35 min, 89% ee;

$[\alpha]_D$=+64.1 (c 0.5, EtOH).

11. Preparation of Compound 11:
(S)-(perfluorophenyl)(pyridine-2-yl)methanol

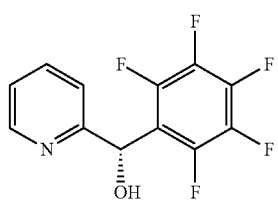 [SMILES: O[C@H](c1ccccn1)c1c(F)c(F)c(F)c(F)c1F]

The same procedure as for Compound 1 was conducted, with the exception of using racemic (perfluorophenyl)(pyridine-2-yl)methanol (275 mg, 1.0 mmol) instead of racemic (4-chlorophenyl)(pyridine-2-yl)methanol (219.7 mg, 1.0 mmol), to prepare Compound 11 (105 mg, 0.38 mmol, 91% ee). HRMS data for the amino alcohol-boron-binol complex are given, together with physicochemical properties of Compound 11, as follows:

HRMS (EI) calculated for $C_{32}H_{17}BF_5NO_3$ [M]$^+$: 569.1222, found: 569.1228;

$^1$H NMR (400 MHz, CDCl$_3$) 8.64-8.58 (m, 2H), 7.81-7.67 (m, 2H), 7.30 (d, 2H), 7.21 (d, J=7.9 Hz, 2H), 6.19 (s, 2H), 5.50 (s, 1H);

$^{13}$C NMR (100 MHz, CDCl$_3$) 157.40, 147.98, 137.33, 123.18, 120.38, 77.35, 77.04, 76.72, 65.58;

HPLC: Chiralpack AD-H column, hexanes:isopropanol=95:5, UV detection at 220 nm, Flow rate 0.8 ml/min, tR (minor isomer)=16.86 min, tR (major isomer)=19.28 min, 91% ee;

$[\alpha]_D$=−10.8 (c 0.75, CHCl$_3$).

12. Preparation of Compound 12: (S)-(3,4-dimethoxyphenyl)(pyridine-2-yl)methanol

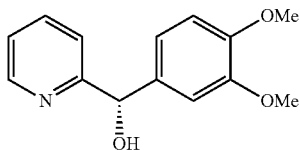 [SMILES: COc1ccc([C@H](O)c2ccccn2)cc1OC]

The same procedure as for Compound 1 was conducted, with the exception of using racemic (3,4-dimethoxyphenyl)(pyridine-2-yl)methanol (245 mg, 1.0 mmol) instead of racemic (4-chlorophenyl)(pyridine-2-yl)methanol (219.7 mg, 1.0 mmol), to prepare Compound 12 (92 mg, 0.375 mmol, 96% ee). HRMS data for the amino alcohol-boron-binol complex are given, together with physicochemical properties of Compound 12, as follows:

HRMS (EI) calculated for $C_{34}H_{26}BNO_5$ [M]$^+$: 539.1904, found: 539.1900;

$^1$H NMR (500 MHz, CDCl$_3$) 8.59-8.54 (m, 1H), 7.67-7.60 (m, 1H), 7.24-7.14 (m, 2H), 6.96-6.91 (m, 1H), 6.91-6.88 (m, 1H), 6.87 6.81 (m, 1H), 5.71 (s, 1H), 5.31 (s, 1H), 3.87 (s, 3H), 3.84 (s, 3H);

$^{13}$C NMR (126 MHz, CDCl$_3$) 161.12, 149.20, 148.72, 147.79, 136.86, 135.84, 122.40, 121.28, 119.58, 110.93, 109.98, 74.82, 55.90, 55.83;

HPLC: Chiralpack AD-H column, hexanes:isopropanol=90:10, UV detection at 220 nm, Flow rate 0.8 ml/min, tR (major isomer)=27.32 min, tR (minor isomer)=28.2 min, 96% ee;

$[\alpha]_D$=−23.2 (c 0.5, EtOH).

13. Preparation of Compound 13: (S)-(2-methylphenyl)(pyrimidine-2-yl)methanol

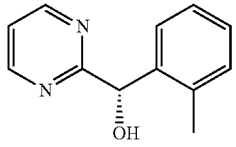

The same procedure as for Compound 1 was conducted, with the exception of using racemic (2-methylphenyl)(pyrimidine-2-yl)methanol (200 mg, 1.0 mmol) instead of racemic (4-chlorophenyl)(pyridine-2-yl)methanol (219.7 mg, 1.0 mmol), to prepare Compound 13 (72 mg, 0.36 mmol, 71% ee). HRMS data for the amino alcohol-boron-binol complex are given, together with physicochemical properties of Compound 13, as follows:

HRMS (EI) calculated for $C_{33}H_{23}BN_2O_3$ [M]$^+$: 494.1802, found: 494.1810;

$^1$H NMR (500 MHz, CDCl$_3$) 8.75 (d, J=4.9 Hz, 2H), 7.25-7.14 (m, 5H), 6.14 (d, J=4.3 Hz, 1H), 4.93 (d, J=4.8 Hz, 1H), 2.53 (s, 3H);

$^{13}$C NMR (126 MHz, CDCl$_3$) 170.23, 156.90, 140.21, 136.46, 130.69, 127.81, 127.22, 126.00, 119.42, 72.89, 19.59;

HPLC: Chiralpack AD-H column, hexanes:isopropanol=95:5, UV detection at 220 nm, Flow rate 0.8 ml/min, tR (minor isomer)=18.18 min, tR (major isomer)=22.48 min, 71% ee;

$[\alpha]_D$=+32.4 (c 0.5, EtOH).

14. Preparation of Compound 14: (S)-(4-(benzyloxy)phenyl)(pyridine-2-yl)methanol

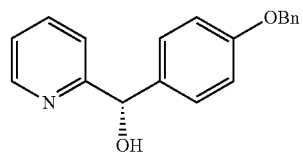 [SMILES: O[C@@H](c1ccc(OCc2ccccc2)cc1)c1ccccn1]

The same procedure as for Compound 1 was conducted, with the exception of using racemic (4-(benzyloxy)phenyl)(pyridine-2-yl)methanol (292 mg, 1.0 mmol) instead of racemic (4-chlorophenyl)(pyridine-2-yl)methanol (219.7 mg, 1.0 mmol), to prepare Compound 14 (118 mg, 0.40 mmol, 96% ee). HRMS data for the amino alcohol-boron-binol complex are given, together with physicochemical properties of Compound 14, as follows:

HRMS (EI) calculated for $C_{39}H_{28}BNO_4$ [M]$^+$: 585.2111, found: 585.2103;

$^1$H NMR (500 MHz, CDCl$_3$) 8.63-8.58 (m, 1H), 7.84 (d, J=1.7 Hz, 1H), 7.74 (dd, J=16.9, 8.7 Hz, 2H), 7.62 (td, J=7.7, 1.7 Hz, 1H), 7.42 (dd, J=8.5, 1.8 Hz, 1H), 7.24-7.15 (m, 3H), 7.15 7.11 (m, 1H), 5.92 (s, 1H), 3.93 (s, 3H);

$^{13}$C NMR (126 MHz, CDCl$_3$) 160.85, 157.70, 147.70, 138.22, 136.82, 134.17, 129.43, 128.74, 128.61, 127.32, 125.97, 125.32, 122.36, 121.42, 118.88, 105.63, 75.03, 55.23;

HPLC: Chiralpack AD-H column, hexanes:isopropanol=90:10, UV detection at 220 nm, Flow rate 0.8 ml/min, tR (minor isomer)=26.34 min, tR (major isomer)=28.37 min, 96% ee;

$[\alpha]_D$=−3.6 (c 0.5, EtOH).

15. Preparation of Compound 15: (S)-(naphthalen-1-yl)(pyridine-2-yl)methanol

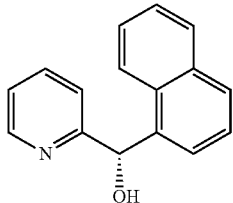 [SMILES: O[C@H](c1ccccn1)c1cccc2ccccc12]

The same procedure as for Compound 1 was conducted, with the exception of using racemic naphthalen-1-yl(pyridine-2-yl)methanol (236 mg, 1.0 mmol) instead of racemic (4-chlorophenyl)(pyridine-2-yl)methanol (219.7 mg, 1.0 mmol), to prepare Compound 15 (90 mg, 0.38 mmol, 87% ee). HRMS data for the amino alcohol-boron-binol complex are given, together with physicochemical properties of Compound 15, as follows:

HRMS (EI) calculated for $C_{36}H_{24}BNO_3$ [M]$^+$: 529.1849, found: 529.1857;

$^1$H NMR (500 MHz, CDCl$_3$) 8.71-8.66 (m, 1H), 8.17-8.10 (m, 1H), 7.93-7.87 (m, 1H), 7.87-7.82 (m, 1H), 7.61-7.55 (m, 1H), 7.55 7.51 (m, 1H), 7.51-7.43 (m, 4H), 7.27-7.21 (m, 1H), 7.11-7.05 (m, 1H), 6.44 (d, J=1.9 Hz, 1H), 5.43 (d, J=3.0 Hz, 1H);

$^{13}$C NMR (100 MHz, CDCl$_3$) 161.16, 147.94, 138.22, 136.94, 134.24, 131.29, 128.80, 128.78, 126.20, 126.17, 125.63, 125.38, 124.47, 122.47, 121.44, 73.62;

HPLC: Chiralpack AD-H column, hexanes:isopropanol=90:10, UV detection at 220 nm, Flow rate 0.8 ml/min, tR (major isomer)=21.32 min, tR (minor isomer)=26.02 min, 87% ee;

[α]$_D$=+64.3 (c 0.75, CHCl$_3$).

16. Preparation of Compound 16: (S)-(6-methoxynaphthalen-2-yl)(pyridine-2-yl)methanol

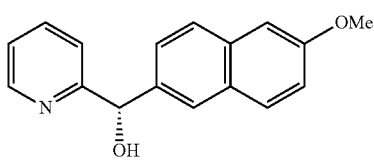 [SMILES: COc1ccc2cc([C@H](O)c3ccccn3)ccc2c1]

The same procedure as for Compound 1 was conducted, with the exception of using racemic (6-methoxynaphthalen-2-yl)(pyridine-2-yl)methanol (265 mg, 1.0 mmol) instead of racemic (4-chlorophenyl)(pyridine-2-yl)methanol (219.7 mg, 1.0 mmol), to prepare Compound 16 (100 mg, 0.376 mmol, 90% ee). HRMS data for the amino alcohol-boron-binol complex are given, together with physicochemical properties of Compound 16, as follows:

HRMS (EI) calculated for $C_{37}H_{26}BNO_4$ [M]$^+$: 559.1955, found: 559.1961;

$^1$H NMR (500 MHz, CDCl$_3$) 8.65-8.60 (m, 1H), 7.86-7.79 (m, 1H), 7.79-7.67 (m, 2H), 7.67-7.60 (m, 1H), 7.44-7.38 (m, 1H), 7.26 7.21 (m, 1H), 7.21-7.15 (m, 2H), 7.14 (d, J=2.5 Hz, 1H), 5.91 (d, J=3.4 Hz, 1H), 5.40 (d, J=4.1 Hz, 1H), 3.94 (s, 3H);

$^{13}$C NMR (126 MHz, CDCl$_3$) 160.85, 157.70, 147.70, 138.22, 136.82, 134.17, 129.43, 128.74, 128.61, 127.32, 125.97, 125.32, 122.36, 121.42, 118.88, 105.63, 75.03, 55.23;

HPLC: Chiralpack AD-H column, hexanes:isopropanol=90:10, UV detection at 220 nm, Flow rate 0.8 ml/min, tR (minor isomer)=31.41 min, tR (major isomer)=36.36 min, 90% ee;

[α]$_D$=−121.2 (c 0.1, CHCl$_3$).

17. Preparation of Compound 17: (S)-(4-(methylthio)phenyl)(pyridine-2-yl)methanol

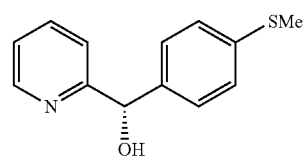 [SMILES: CSc1ccc([C@H](O)c2ccccn2)cc1]

The same procedure as for Compound 1 was conducted, with the exception of using racemic (4-(methylthio)phenyl)(pyridine-2-yl)methanol (232 mg, 1.0 mmol) instead of racemic (4-chlorophenyl)(pyridine-2-yl)methanol (219.7 mg, 1.0 mmol), to prepare Compound 17 (86 mg, 0.37 mmol, 78% ee). HRMS data for the amino alcohol-boron-binol complex are given, together with physicochemical properties of Compound 17, as follows:

HRMS (EI) calculated for $C_{33}H_{24}BNO_3S$ [M]$^+$: 525.1570, found: 525.1578;

$^1$H NMR (500 MHz, CDCl$_3$) 8.59-8.54 (m, 1H), 7.67-7.60 (m, 1H), 7.34-7.28 (m, 2H), 7.26-7.18 (m, 3H), 7.17 (d, J=7.9 Hz, 1H), 5.74 (s, 1H), 2.47 (s, 3H);

$^{13}$C NMR (100 MHz, CDCl$_3$) 160.81, 147.88, 140.19, 138.03, 136.89, 127.60, 126.77, 122.49, 121.31, 74.60, 15.87;

HPLC: Chiralpack AD-H column, hexanes:isopropanol=90:10, UV detection at 220 nm, Flow rate 0.8 ml/min, tR (minor isomer)=22.7 min, tR (major isomer)=26.08 min, 78% ee;

[α]$_D$=−15.4 (c 1.0, CHCl$_3$).

18. Preparation of Compound 18: (S)-(3-nitrophenyl)(pyridine-2-yl)methanol

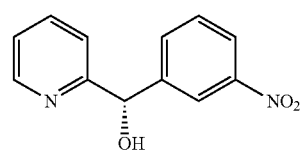 [SMILES: O=[N+]([O-])c1cccc([C@H](O)c2ccccn2)c1]

The same procedure as for Compound 1 was conducted, with the exception of using racemic (3-nitrophenyl)(pyridine-2-yl)methanol (230 mg, 1.0 mmol) instead of racemic (4-chlorophenyl)(pyridine-2-yl)methanol (219.7 mg, 1.0 mmol), to prepare Compound 18 (81.2 mg, 0.35 mmol, 82% ee). HRMS data for the amino alcohol-boron-binol complex are given, together with physicochemical properties of Compound 18, as follows:

HRMS (EI) calcd for $C_{32}H_{21}BN_2O_5$ [M]$^+$: 524.1544, found: 524.1551;

¹H NMR (400 MHz, CDCl₃) 8.55-8.48 (m, 1H), 8.31-8.24 (m, 1H), 8.14-8.05 (m, 1H), 7.82-7.72 (m, 1H), 7.72-7.62 (m, 1H), 7.48 (t, J=7.9 Hz, 1H), 7.28-7.18 (m, 2H), 5.87 (s, 1H), 5.72 (s, 1H);

¹³C NMR (100 MHz, CDCl₃) 159.87, 148.35, 148.28, 145.43, 137.39, 133.05, 129.51, 123.06, 122.70, 121.79, 121.23, 74.23;

HPLC: Chiralpack AD-H column, hexanes:isopropanol=90:10, UV detection at 220 nm, Flow rate 0.8 ml/min, tR (minor isomer)=17.36 min, tR (major isomer)=20.72 min, 82% ee;

$[\alpha]_D$=−21.6 (c 1.25, CHCl₃).

19. Preparation of Compound 19: (S)-(2,5-dimethoxyphenyl)(pyridine-2-yl)methanol

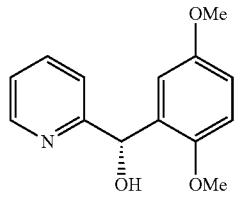 [SMILES: COc1ccc(OC)c([C@H](O)c2ccccn2)c1]

The same procedure as for Compound 1 was conducted, with the exception of using racemic (2,5-dimethoxyphenyl)(pyridine-2-yl)methanol (245 mg, 1.0 mmol) instead of racemic (4-chlorophenyl)(pyridine-2-yl)methanol (219.7 mg, 1.0 mmol), to prepare Compound 19 (95 mg, 0.389 mmol, 63% ee). HRMS data for the amino alcohol-boron-binol complex are given, together with physicochemical properties of Compound 19, as follows:

HRMS (EI) calcd for $C_{34}H_{26}BNO_5$ [M]⁺: 539.1904, found: 539.1551;

¹H NMR (400 MHz, CDCl₃) 8.59-8.48 (m, 1H), 7.64-7.56 (m, 1H), 7.34-7.28 (m, 1H), 7.20-7.12 (m, 1H), 6.98-6.91 (m, 1H), 6.89 6.82 (m, 1H), 6.82-6.74 (m, 1H), 6.20 (s, 1H), 5.37 (s, 1H), 3.83 (s, 3H), 3.73 (s, 3H);

¹³C NMR (100 MHz, CDCl₃) 161.05, 153.92, 150.88, 147.71, 136.74, 132.86, 122.27, 121.28, 113.52, 113.32, 112.07, 69.01, 56.18, 55.66;

HPLC: Chiralpack AD-H column, hexanes:isopropanol=95:5, UV detection at 220 nm, Flow rate 0.8 ml/min, tR (minor isomer)=26.6 min, tR (major isomer)=29.3 min, 63% ee;

$[\alpha]_D$=−83.0 (c 0.5, EtOH).

20. Preparation of Compound 20: (1S)-1-phenyl-1-(pyridine-2-yl)ethan-1-ol

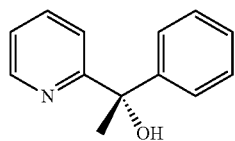

The same procedure as for Compound 1 was conducted, with the exception of using racemic 1-phenyl-1-(pyridine-2-yl)ethan-1-ol (200 mg, 1.0 mmol) instead of racemic (4-chlorophenyl)(pyridine-2-yl)methanol (219.7 mg, 1.0 mmol), to prepare Compound 20 (72 mg, 0.36 mmol, 99% ee). HRMS data for the amino alcohol-boron-binol complex are given, together with physicochemical properties of Compound 20, as follows:

HRMS (EI) calcd for $C_{32}H_{21}BN_2O_5$ [M]⁺: 493.1849, found: 493.1849;

¹H NMR (400 MHz, CDCl₃) 8.58-8.52 (m, 1H), 7.71-7.61 (m, 1H), 7.59-7.50 (m, 2H), 7.43-7.30 (m, 3H), 7.31-7.24 (m, 1H), 7.28 7.13 (m, 2H), 5.92 (d, J=2.2 Hz, 1H), 1.98 (s, 2H);

¹³C NMR (100 MHz, CDCl₃) 164.83, 147.44, 147.22, 137.03, 128.25, 127.01, 125.95, 122.08, 120.34, 77.50, 77.18, 76.86, 75.15, 29.31;

HPLC: Chiralpack AD-H column, hexanes:isopropanol=95:5, UV detection at 220 nm, Flow rate 0.5 ml/min, tR (minor isomer)=19.2 min, tR (major isomer)=20.6 min, 99% ee;

$[\alpha]_D$=+21.6 (c 1.5, CHCl₃).

21. Preparation of Compound 21: (S)-1-(4-chlorophenyl)-1-(pyridine-2-yl)ethan-1-ol

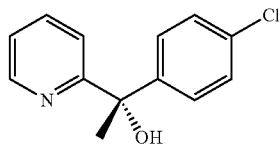 [SMILES: C[C@](O)(c1ccc(Cl)cc1)c1ccccn1]

The same procedure as for Compound 1 was conducted, with the exception of using racemic 1-(4-chlorophenyl)-1-(pyridine-2-yl)ethan-1-ol (234 mg, 1.0 mmol) instead of racemic (4-chlorophenyl)(pyridine-2-yl)methanol (219.7 mg, 1.0 mmol), to prepare Compound 21 (95 mg, 0.36 mmol, 57% ee). HRMS data for the amino alcohol-boron-binol complex are given, together with physicochemical properties of Compound 21, as follows:

HRMS (EI) calcd for $C_{33}H_{23}BClNO_3$ [M]⁺: 527.1460, found: 527.1457;

¹H NMR (400 MHz, CDCl₃) 8.57-8.51 (m, 1H), 7.75-7.63 (m, 1H), 7.51-7.41 (m, 2H), 7.36-7.26 (m, 3H), 7.25-7.17 (m, 1H), 5.88 (d, J=1.8 Hz, 1H), 1.93 (s, 3H);

¹³C NMR (100 MHz, CDCl₃) 164.27, 147.55, 145.82, 137.15, 132.86, 128.32, 127.46, 122.26, 120.16, 77.43, 77.11, 76.79, 74.81, 29.22;

The ee was determined by HPLC with CHIRAL AD C18 Column (5 m, 4.6 150 mm) (Hexanes:IPA=95:5, UV detection at 220 nm, Flow rate 0.5 ml/min) tR (minor isomer)=19.2 min, tR (major isomer)=20.6 min, 57% ee;

$[\alpha]_D$=+12.4 (c 1.5, CHCl₃).

22. Preparation of Compound 22: (S)-2-methyl-1-(pyridine-2-yl)propan-1-ol

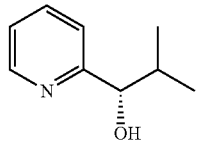

The same procedure as for Compound 1 was conducted, with the exception of using racemic 2-methyl-1-(pyridine-2-yl)propan-1-ol (152 mg, 1.0 mmol) instead of racemic (4-chlorophenyl)(pyridine-2-yl)methanol (219.7 mg, 1.0 mmol), to prepare Compound 22 (57 mg, 0.376 mmol, 71% ee). HRMS data for the amino alcohol-boron-binol complex are given, together with physicochemical properties of Compound 22, as follows:

HRMS (EI) calcd for $C_{29}H_{24}BNO_3$ [M]+: 445.1849, found: 445.1854;

$^1$H NMR (400 MHz, CDCl$_3$) 8.76-8.28 (m, 1H), 7.87-7.47 (m, 1H), 7.47-7.03 (m, 2H), 4.84-4.24 (m, 2H), 2.14-1.81 (m, 1H), 1.14 0.84 (m, 3H), 0.84-0.54 (m, 3H);

$^{13}$C NMR (100 MHz, CDCl$_3$) 161.56, 147.97, 122.15, 121.03, 77.40, 35.04, 19.40, 16.20;

HPLC: after acylation, CHIRAL OJ column, Hexanes:IPA=97:03, UV detection at 254 nm, Flow rate 0.3 ml/min, tR (minor isomer)=22.02 min, tR (major isomer)=25.35 min, 71% ee;

$[\alpha]_D$=+28.6 (c 0.5, EtOH).

23. Preparation of Compound 23: (S)-1-(pyridine-2-yl)but-3-en-1-ol

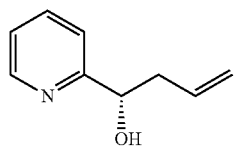

The same procedure as for Compound 1 was conducted, with the exception of using racemic 1-(pyridine-2-yl)but-3-en-1-ol (150 mg, 1.0 mmol) instead of racemic (4-chlorophenyl)(pyridine-2-yl)methanol (219.7 mg, 1.0 mmol), to prepare Compound 23 (57 mg, 0.382 mmol, 68% ee). HRMS data for the amino alcohol-boron-binol complex are given, together with physicochemical properties of Compound 23, as follows:

HRMS (EI) calcd for $C_{29}H_{22}BNO_3$ [M]+: 443.1693, found: 443.1691;

$^1$H NMR (400 MHz, CDCl$_3$) 8.38-8.31 (m, 2H), 7.58-7.48 (m, 2H), 7.26-7.22 (m, 1H), 7.06-6.98 (m, 2H), 5.78-5.63 (m, 2H), 5.00 4.92 (m, 1H), 4.96-4.89 (m, 3H), 4.85-4.73 (m, 2H), 4.73-4.66 (m, 2H), 2.56-2.45 (m, 2H), 2.43-2.32 (m, 2H);

$^{13}$C NMR (100 MHz, CDCl$_3$) 162.26, 162.22, 148.11, 136.64, 134.27, 122.18, 120.43, 117.61, 117.59, 117.57, 72.73, 42.61, 42.58.

HPLC: after acylation, with CHIRAL OD, Hexanes:IPA=90:10, UV detection at 254 nm, Flow rate 0.5 ml/min, tR (major isomer)=9.92 min, tR (major isomer)=13.02 min, 68% ee;

$[\alpha]_D$=−14.8 (c 1.5, CHCl$_3$).

23-1. Preparation of Compound 23: (S)-1-(pyridine-2-yl)but-3-en-1-ol

The same procedure as for Compound 1 was conducted, with the exception of using 0.45 equivalents of (R)-3,3′-(CONEt$_2$)$_2$-binol (218 mg) instead of (R)-binol (128 mg, 0.45 mmol), to prepare Compound 23 at a yield of 39% and an ee of 86%.

$[\alpha]_{DH}$=−18.9 (c 1.0, CHCl$_3$).

24. Preparation of Compound 24: (S)-1-phenyl-2-(piperidin-1-yl)ethan-1-ol

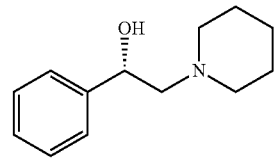 [SMILES: O[C@H](CN1CCCCC1)c1ccccc1]

The same procedure as for Compound 1 was conducted, with the exception of using racemic 1-phenyl-2-(piperidin-1-yl)ethan-1-ol (205 mg, 1.0 mmol) instead of racemic (4-chlorophenyl)(pyridine-2-yl)methanol (219.7 mg, 1.0 mmol), to prepare Compound 24 (76.5 mg, 0.37 mmol, 77% ee). HRMS data for the amino alcohol-boron-binol complex are given, together with physicochemical properties of Compound 24, as follows:

HRMS (EI) calcd for $C_{33}H_{30}BNO_3$ [M]+: 499.2319, found: 499.2323;

$^1$H NMR (500 MHz, CDCl$_3$) 7.43-7.15 (m, 5H), 4.78-4.65 (m, 1H), 3.29 (s, 1H), 2.75-2.71 (m, 1H), 2.55-2.48 (m, 1H), 2.47-2.38 (m, 3H), 1.75-1.57 (m, 4H), 1.53-1.47 (m, 2H), 1.30-1.27 (m, 1H), 0.98-0.83 (m, 1H);

$^{13}$C NMR (126 MHz, CDCl$_3$) 142.45, 128.32, 127.39, 125.87, 68.67, 66.93, 54.47, 26.12, 24.27;

HPLC: CHIRAL OD column, Hexanes:IPA:DEA=95:05:0.5, UV detection at 254 nm, Flow rate 1.0 ml/min, tR (minor isomer)=11.66 min, tR (major isomer)=15.47 min, 77% ee;

$[\alpha]_D$=+30.4 (c 1.25, EtOH).

25. Preparation of Compound 25: (S)-2-morpholino-1-phenylethan-1-ol

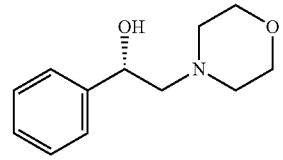 [SMILES: O[C@H](CN1CCOCC1)c1ccccc1]

The same procedure as for Compound 1 was conducted, with the exception of using racemic 2-morpholino-1-phenylethan-1-ol (207.5 mg, 1.0 mmol) instead of racemic (4-chlorophenyl)(pyridine-2-yl)methanol (219.7 mg, 1.0 mmol), to prepare Compound 25 (85 mg, 0.38 mmol, 91% ee). HRMS data for the amino alcohol-boron-binol complex are given, together with physicochemical properties of Compound 25, as follows:

HRMS (EI) calcd for $C_{32}H_{28}BNO_4$ [M]+: 501.2111, found: 501.2117;

$^1$H NMR (500 MHz, CDCl$_3$) 7.43-7.34 (m, 4H), 7.34-7.27 (m, 1H), 4.82-4.75 (m, 1H), 3.84-3.72 (m, 4H), 2.81-2.73 (m, 2H), 2.60 2.54 (m, 1H), 2.54-2.45 (m, 3H);

$^{13}$C NMR (126 MHz, CDCl$_3$) 141.88, 128.41, 127.61, 125.86, 68.60, 68.17, 67.05, 66.71;

HPLC: CHIRAL OD C$_{18}$ Column (5 m, 4.6 150 mm) (Hexanes:IPA:DEA=95:05:0.5, UV detection at 254 nm, Flow rate 1.0 ml/min, tR (major isomer)=21.81 min, tR (major isomer)=29.29 min, 91% ee;

$[\alpha]_D$=+45.3 (c 0.9, EtOH).

26. Preparation of Compound 26: (R)-1-(phenyl (pyrrolidin-1-yl)methyl)naphthalen-2-ol

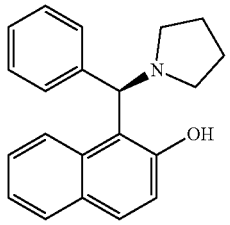 [SMILES: Oc1ccc2ccccc2c1[C@@H](c1ccccc1)N1CCCC1]

The same procedure as for Compound 1 was conducted, with the exception of using racemic 1-(phenyl(pyrrolidin-1-yl)methyl)naphthalen-2-ol (303.5 mg, 1.0 mmol) instead of racemic (4-chlorophenyl)(pyridine-2-yl)methanol (219.7 mg, 1.0 mmol), to prepare Compound 26 (96 mg, 0.31 mmol, 78% ee). HRMS data for the amino alcohol-boron-binol complex are given, together with physicochemical properties of Compound 26, as follows:

HRMS (EI) calculated for C$_{41}$H$_{32}$BNO$_3$ [M]$^+$: 597.2475, found: 597.2451;

$^1$H NMR (300 MHz, CDCl$_3$), δ 7.87 (d, J=8.6 Hz, 1H), 7.77-7.53 (m, 4H), 7.43-7.32 (m, 1H), 7.31-7.11 (m, 5H), 5.13 (s, 1H), 3.56-2.91 (br s, 1H), 2.91-2.05 (m, 3H), 1.98-1.61 (m, 4H);

$^{13}$C NMR (75 MHz, CDCl$_3$), δ 155.9, 141.3, 132, 129.4, 128.9, 128.8, 128.6, 128.5, 127.9, 126.5, 122.4, 121.2, 119.9, 116.6, 70.8, 53.5, 23;

HPLC: CHIRAL OD column, hexanes:IPA=90:10, UV detection at 254 nm, Flow rate 1.0 ml/min, tR (major isomer)=5.26 min, tR (minor isomer)=5.85 min, 78% ee;

$[\alpha]_D$=−69.8 (c 1.5, CHCl$_3$).

27. Preparation of Compound 27: (R)-1-(morpholino(phenyl)methyl)naphthalen-2-ol

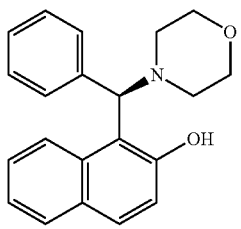 [SMILES: Oc1ccc2ccccc2c1[C@@H](c1ccccc1)N1CCOCC1]

The same procedure as for Compound 1 was conducted, with the exception of using racemic 1-(morpholino(phenyl)methyl)naphthalen-2-ol (320 mg, 1.0 mmol) instead of racemic (4-chlorophenyl)(pyridine-2-yl)methanol (219.7 mg, 1.0 mmol), to prepare Compound 27 (100 mg, 0.31 mmol, 99% ee). HRMS data for the amino alcohol-boron-binol complex are given, together with physicochemical properties of Compound 27, as follows:

HRMS (EI) calculated for C$_{41}$H$_{32}$BNO$_4$ [M]$^+$: 613.2424, found: 597.2451;

$^1$H NMR (400 MHz, CDCl$_3$) 13.15 (s, 1H), 7.88 (d, J=8.6 Hz, 1H), 7.77-7.68 (m, 2H), 7.64-7.57 (m, 2H), 7.46-7.37 (m, 1H), 7.36-7.21 (m, 5H), 7.18 (d, J=8.8 Hz, 1H), 5.16 (s, 1H), 4.08 3.77 (m, 3H), 3.77-3.48 (m, 1H), 3.38-2.98 (m, 1H), 2.61-2.40 (m, 3H);

$^{13}$C NMR (100 MHz, CDCl$_3$) 154.79, 138.68, 132.38, 129.81, 128.95, 128.85, 128.24, 126.59, 122.65, 121.06, 119.82, 115.14, 77.36, 77.04, 76.73, 72.06, 66.93; HPLC: CHIRAL OD-H Column, Hexanes:IPA=90:10, UV wavelength at 254 nm, Flow rate=1.0 ml/min, tR (major isomer)=9.48 min, tR (minor isomer)=10.82 min, 99% ee;

$[\alpha]_D$=−102.4 (c 1.25, CHCl$_3$).

28. Preparation of Compound 28: (S)-3-(dimethylamino)-1-(thiophen-2-yl)propan-1-ol

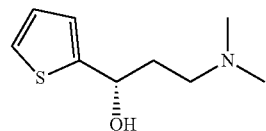

The same procedure as for Compound 1 was conducted, with the exception of using racemic 3-(dimethylamino)-1-(thiophen-2-yl)propan-1-ol (186 mg, 1.0 mmol) and (R)-3,3'-(CONEt$_2$)$_2$-binol (218 mg, 0.45 mmol) instead of racemic (4-chlorophenyl) (pyridine-2-yl)methanol (219.7 mg, 1.0 mmol) and (R)-binol (128 mg, 0.45 mmol), respectively, to prepare Compound 28 (65 mg, 0.35 mmol, 62% ee). HRMS data for the amino alcohol-boron-binol complex are given, together with physicochemical properties of Compound 28, as follows:

HRMS (EI) calculated for C$_{39}$H$_{44}$BN$_3$O$_5$S [M]$^+$: 677.3095, found: 677.3097;

$^1$H NMR (500 Hz, CDCl$_3$) δ 7.21 (d, J=4.8 Hz, 1H), 6.98-6.80 (m, 2H), 5.19 (dd, J=4.0 Hz, 8.0 Hz, 1H), 2.70-2.50 (m, 2H), 2.29 (s, 6H), 2.00-1.88 (m, 2H);

$^{13}$C NMR (126 MHz, CDCl$_3$) δ 150.80, 126.45, 123.85, 122.56, 67.46, 56.02, 45.24, 36.94;

HPLC: Chiralcel AD-H column, hexane:isopropanol:diethylamine=97:2:0.1, Flow rate=0.5 ml/min, UV detection at 254 nm, tR (major isomer)=25.65 min, tR (minor isomer)=27.94 min, 62% ee;

$[\alpha]_D$=−4.6 (c 0.5, MeOH).

29. Preparation of Compound 29: (S)-3-(dimethylamino)-1-phenylpropan-1-ol

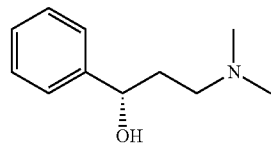

The same procedure as for Compound 28 was conducted, with the exception of using racemic 3-(dimethylamino)-1-phenylpropan-1-ol (180 mg, 1.0 mmol) instead of racemic (4-chlorophenyl)(pyridine-2-yl)methanol (219.7 mg, 1.0 mmol), to prepare Compound 29 (60 mg, 0.33 mmol, 81% ee). HRMS data for the amino alcohol-boron-binol complex are given, together with physicochemical properties of Compound 29, as follows:

HRMS (EI) calculated for $C_{41}H_{46}BN_3O_5$ [M]$^+$: 671.3531, found: 671.3537;

$^1$H NMR (400 MHz, CDCl$_3$): 7.39 (m, 4H), 7.24 (t, 1H, J=7.08 Hz), 5.26 (s, 1H), 4.94 (q, J=4.12 Hz, 1H), 2.63 (m, 1H), 2.43 (m, 1H), 2.29 (s, 6H), 1.84 (m, 2H);

$^{13}$C NMR (100 MHz, CDCl$_3$): 145.13, 128.12, 126.72, 125.51, 75.50, 58.30, 45.24, 34.57;

HPLC: Chiralcel AD-H column, hexane:isopropanol:diethylamine=95:5:0.2, UV detection at 254 nm, Flow rate 0.5 ml/min, tR (major isomer)=13.33 min, tR (minor isomer)=18.47 min, 81% ee;

$[\alpha]_D$=−25.6 (c 0.5, MeOH).

30. Preparation of Compound 30: (S)-3-(dimethylamino)-3-phenylpropan-1-ol

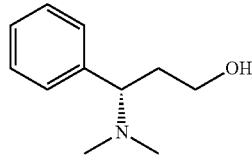

The same procedure as for Compound 1 was conducted, with the exception of using racemic 3-(dimethylamino)-3-phenylpropan-1-ol (180 mg, 1.0 mmol) instead of racemic (4-chlorophenyl)(pyridine-2-yl)methanol (219.7 mg, 1.0 mmol), to prepare Compound 30 (58 mg, 0.32 mmol, 95% ee). HRMS data for the amino alcohol-boron-binol complex are given, together with physicochemical properties of Compound 30, as follows:

HRMS (EI) calculated for $C_{31}H_{28}BNO_3$ [M]$^+$: 473.2162, found: 473.2157;

$^1$H NMR (400 MHz, CDCl$_3$): 7.32 (m, 5H), 5.14 (brs, 1H), 3.85 (m, 2H), 3.72 (m, 1H), 2.40 (m, 1H), 2.19 (s, 6H), 1.74 (m, 1H);

$^{13}$C NMR (100 MHz, CDCl$_3$): 136.1, 129.3, 128.2, 127.9, 127.0, 71.0, 63.3, 41, 7, 32.2;

HPLC: Chiralcel OJ column, hexane:isopropanol:diethylamine=90:10:0.1, UV detection at 254 nm, Flow rate 1.0 ml/min, tR (major isomer)=12.10 min, tR (minor isomer)=19.71 min, 94% ee;

$[\alpha]_D$=+38.5 (c 1.0, CHCl$_3$).

31. Preparation of Compound 31: (S)-1-(2-(dimethylamino)-1-(4-methoxyphenyl)ethyl)cyclohexanol

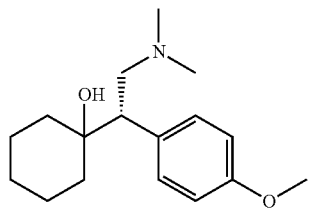 [SMILES: COc1ccc([C@@H](CN(C)C)C2(O)CCCCC2)cc1]

The same procedure as for Compound 1 was conducted, with the exception of using isopropanol (6 ml), racemic 1-(2-(dimethylamino)-1-(4-methoxyphenyl)ethyl)cyclohexanol (277.4 mg, 1.0 mmol), and (R)-3,3'-(CONEt$_2$)$_2$-binol (218 mg, 0.45 mmol) instead of acetonitrile (6 ml), racemic (4-chlorophenyl)(pyridine-2-yl)methanol (219.7 mg, 1.0 mmol), and (R)-binol (128 mg, 0.45 mmol), respectively, to prepare Compound 31 (86 mg, 0.31 mmol, 71% ee). HRMS data for the amino alcohol-boron-binol complex are given, together with physicochemical properties of Compound 31, as follows:

HRMS (EI) calculated for $C_{47}H_{56}BN_3O_6$ [M]$^+$: 769.4262, found: 769.4260;

$^1$H NMR (500 MHz, Acetonitrile-d$_3$) $\delta_H$ 7.13 (d, J=8.3 Hz, 2H), 6.86 (d, J=8.3 Hz, 2H), 3.78 (s, 3H), 3.25 (t, J=12.0 Hz, 1H), 2.93 (dd, J=11.3, 4.5 Hz, 1H), 2.28 (s, 7H), 1.65 (pt, J=12.8, 3.6 Hz, 3H), 1.57-1.44 (m, 3H), 1.35 (dt, J=12.9, 3.8 Hz, 1H), 1.25 (td, J=13.4, 4.1 Hz, 1H), 1.02-0.83 (m, 2H) ppm;

HPLC: Chiral AD-H, 3% IPA in Hexanes, 0.1% TEA, Flow rate 0.4 ml/min, UV detection at 274 nm, tR=13.97 is =16.13 (Major), 71% ee; $[\alpha]_D$=+28.4 (c 1.05, EtOH).

Comparative Example 1: Preparation of Comparative Optically Active Amino Alcohol Derivatives 1. Preparation of Comparative Compound 1: (S)-(4-chlorophenyl)(pyridine-2-yl)methanol The same procedure as for Compound 1 was conducted, with the exception of using 1 equivalent of B(OH)$_3$ and 1 equivalent of (R)-binol instead of B(OiPr)$_3$ (188 mg, 1.0 mmol) and (R)-binol (128 mg, 0.45 mmol), respectively, to prepare Comparative Compound 1 at a yield of 64% and an ee of 28%.

2. Preparation of Comparative Compound 2: (S)-(4-chlorophenyl)(pyridine-2-yl)methanol The same procedure as for Compound 1 was conducted, with the exception of using 1 equivalent of (R)-binol instead of (R)-binol (128 mg, 0.45 mmol), to prepare Comparative Compound 2 at a yield of 52% and an ee of 38% ee.

3. Preparation of Comparative Compound 3: (S)-(4-chlorophenyl)(pyridine-2-yl)methanol The same procedure as for Compound 1 was conducted, with the exception of using 1 equivalent of B(OH)$_3$ and 0.5 equivalents of (R)-binol instead of B(OiPr)$_3$ (188 mg, 1.0 mmol) and (R)-binol (128 mg, 0.45 mmol), respectively, to prepare Comparative Compound 3 at a yield of 42% and an ee of 62% ee.

4. Preparation of Comparative Compound 4: (S)-(4-chlorophenyl)(pyridine-2-yl)methanol The same procedure as for Compound 1 was conducted, with the exception of using 1 equivalent of B(OMe)$_3$ and 0.5 equivalents of (R)-binol instead of B(OiPr)$_3$ (188 mg, 1.0 mmol) and (R)-binol (128 mg, 0.45 mmol), respectively, to prepare Comparative Compound 4 at a yield of 38% and an ee of 65% ee.

5. Preparation of Comparative Compound 5: (S)-(4-chlorophenyl)(pyridine-2-yl)methanol The same procedure as for Compound 1 was conducted, with the exception of using 1 equivalent of B(OEt)$_3$ and 0.5 equivalents of (R)-binol instead of B(OiPr)₃ (188 mg, 1.0 mmol) and (R)-binol (128 mg, 0.45 mmol), respectively, to prepare Comparative Compound 5 at a yield of 45% and an ee of 73% ee.

6. Preparation of Comparative Compound 6: (S)-(4-chlorophenyl)(pyridine-2-yl)methanol The same procedure as for Compound 1 was conducted, with the exception of using 1 equivalent of B(OPh)₃ and 0.5 equivalents of (R)-binol instead of B(OiPr)₃ (188 mg, 1.0 mmol) and (R)-binol (128 mg, 0.45 mmol), respectively, to prepare Comparative Compound 6 at a yield of 39% and an ee of 67% ee.

7. Preparation of Comparative Compound 7: (S)-(4-chlorophenyl)(pyridine-2-yl)methanol The same procedure as for Compound 1 was conducted, with the exception of using 0.5 equivalents of (R)-3,3'-Br₂-binol instead of (R)-binol (128 mg, 0.45 mmol), to prepare Comparative Compound 7 at a yield of 40% and an ee of 60% ee.

Experimental Example 1: Identification of Optical Purity

Optical purities of Amino alcohol derivatives for the compounds prepared in Example 1 and Comparative Example 1 are given in Table 1, below.

TABLE 1

| Compound | Reaction Condition Boron Compound | (R)- or (S)-Binol | Optical Purity (% ee) |
|---|---|---|---|
| Example 1 - Compound 1 | 1 eq, B(OPrⁱ)₃ | (R)-binol structure | 98 |
| Comparative Example 1 - Comparative Compound 1 | 1 eq, B(OH)₃ | (R)-binol structure | 28 |
| Comparative Example 1 - Comparative Compound 2 | 1 eq, B(OPrⁱ)₃ | (S)-binol structure | 38 |
| Comparative Example 1 - Comparative Compound 3 | 1 eq, B(OH)₃ | (R)-binol structure | 62 |
| Comparative Example 1 - Comparative Compound 4 | 1 eq, B(OMe)₃ | (R)-binol structure | 65 |
| Comparative Example 1 - Comparative Compound 5 | 1 eq, B(OEt)₃ | (R)-binol structure | 73 |
| Comparative Example 1 - Comparative Compound 6 | 1 eq, B(OPh)₃ | (R)-binol structure | 67 |
| Comparative Example 1 - Comparative Compound 7 | 1 eq, B(OMe)₃ | (R)-3,3'-Br₂-binol structure | 60 |

As is understood from the data of Table 1, Compound 1, which was prepared under the condition of Example 1, is for superior in terms of optical purify to Comparative Compounds 1 to 7, which were prepared under the condition of Comparative Example 1.

Accordingly, amino alcohol derivatives with high optical purity can be obtained by reacting a racemic compound with a boron compound and (R)- or (S)-binol at specific equivalents controlled according to the present disclosure.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method for preparing an optically active amino alcohol derivative from a racemic amino alcohol, the method comprising:
   a first step for adding a racemic compound represented by any of the following Chemical Formula 1 with a boron compound, a (R)- or (S)-binol, and a solvent to form an amino alcohol-boron-binol complex represented by any one of the following Chemical Formula 3 as a precipitate; and
   a second step for hydrolyzing the precipitate of the first step to obtain an optically active amino alcohol derivative:

[Chemical Formula 1]

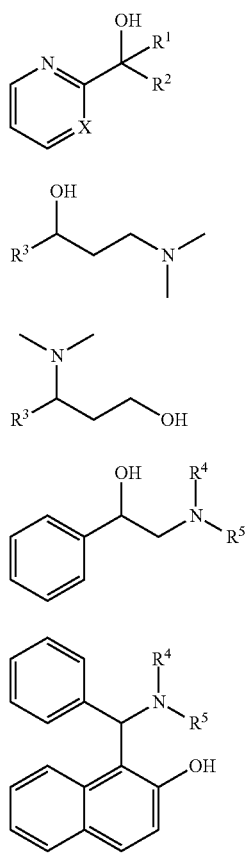

1-1

1-2

1-3

1-4

1-5

1-6

[Chemical Formula 3]

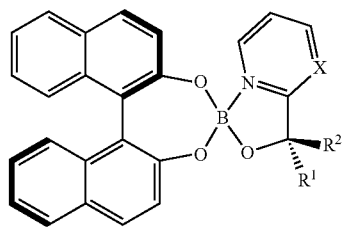

3-1-1

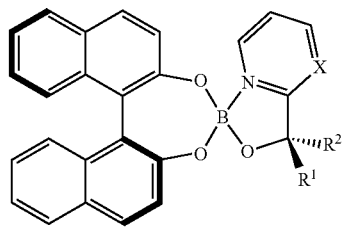

3-1-2

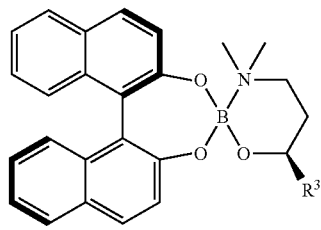

3-2-1

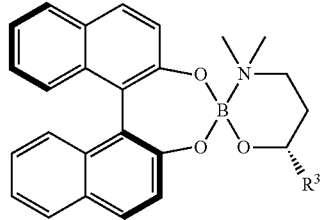

3-2-2

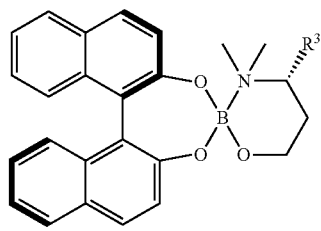

3-3-1

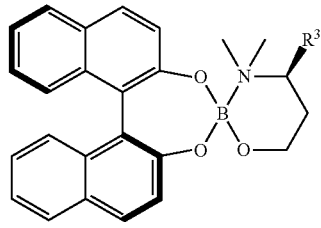

3-3-2

3-4-1

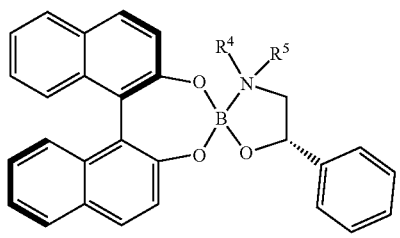

3-4-2

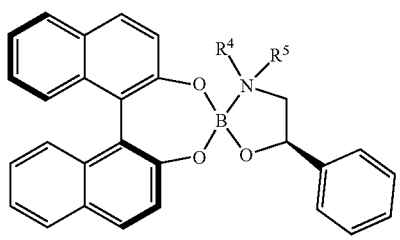

3-5-1

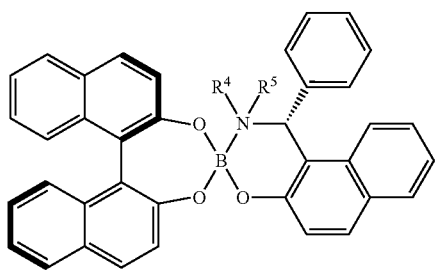

3-5-2

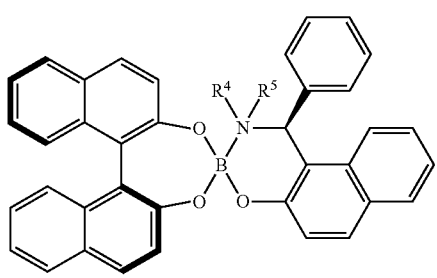

3-6-1

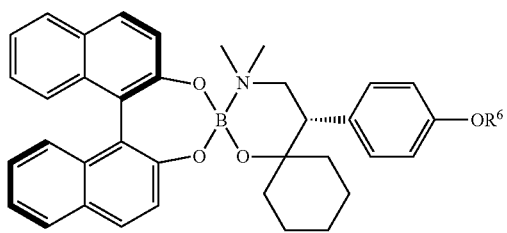

3-6-2

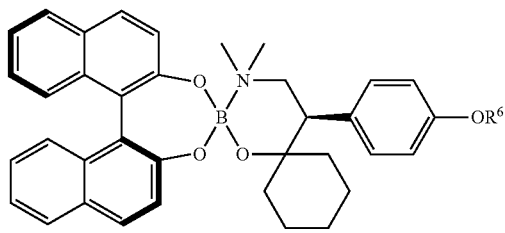

wherein, in the Chemical Formulae 1 and 3,

X is CH, C—CH$_3$ or N;

R$^1$ is a hydrogen or a C$_1$-C$_{10}$ alkyl substituent;

R$^2$ is a substituent selected from the group consisting of a substituted or unsubstituted C$_1$-C$_{10}$ alkyl, a substituted or unsubstituted C$_2$-C$_{10}$ alkenyl, a substituted or unsubstituted C$_2$-C$_{10}$ alkynyl, a substituted or unsubstituted phenyl, a substituted or unsubstituted naphthyl, a substituted or unsubstituted pyrrolyl, a substituted or unsubstituted furanyl, a substituted or unsubstituted pyridinyl, a substituted or unsubstituted pyrimidinyl, and a substituted or unsubstituted pyranyl, wherein the substituted alkyl, alkenyl, alkynyl, phenyl, naphthyl, pyrrolyl, furanyl, pyridinyl, pyrimidinyl, or pyranyl has at least one substituent selected from the group consisting of hydrogen, halogen, hydroxy, amino, cyano, nitro, —S—(C$_1$-C$_{10}$ alkyl), C$_1$-C$_{10}$ haloalkyl, C$_1$-C$_{10}$ alkyl, benzyloxy, and C$_1$-C$_{10}$ alkoxy;

R$^3$ is a substituent selected from the group consisting of a substituted or unsubstituted phenyl, a substituted or unsubstituted thiophenyl, a substituted or unsubstituted pyrrolyl, a substituted or unsubstituted furanyl, a substituted or unsubstituted pyridinyl, a substituted or unsubstituted pyrimidinyl, and a substituted or unsubstituted pyranyl, wherein the substituted phenyl, thiophenyl, pyrrolyl, furanyl, pyridinyl, pyrimidinyl, or pyranyl has at least one substituent selected from the group consisting of hydrogen, halogen, hydroxy, amino, cyano, nitro, —S—(C$_1$-C$_{10}$ alkyl), C$_1$-C$_{10}$ haloalkyl, C$_1$-C$_{10}$ alkyl, and C$_1$-C$_{10}$ alkoxy;

R$^4$ and R$^5$ are each independently a substituent selected from the group consisting of a substituted or unsubstituted C$_1$-C$_{10}$ alkyl, a substituted or unsubstituted pyrrolyl, a substituted or unsubstituted furanyl, a substituted or unsubstituted pyridinyl, a substituted or unsubstituted pyrimidinyl, and a substituted or unsubstituted pyranyl, wherein the substituted alkyl, pyrrolyl, furanyl, pyridinyl, pyrimidinyl, or pyranyl has at least one substituent selected from the group consisting of hydrogen, halogen, hydroxy, amino, cyano, nitro, —S—(C$_1$-C$_{10}$ alkyl), C$_1$-C$_{10}$ haloalkyl, C$_1$-C$_{10}$ alkyl, and C$_1$-C$_{10}$ alkoxy; or R$^4$ and R$^5$ form together a substituted or unsubstituted C$_4$-C$_{12}$ heterocycloalkyl, wherein the substituted heterocycloalkyl has at least one substituent selected from the group consisting of hydrogen, halogen, hydroxy, amino, cyano, nitro, —S—(C$_1$-C$_{10}$ alkyl), C$_1$-C$_{10}$ haloalkyl, C$_1$-C$_{10}$ alkyl, and C$_1$-C$_{10}$ alkoxy; and R$^6$ is a substituent selected from the group consisting of hydrogen, and a substituted or unsubstituted C$_1$-C$_{10}$ alkyl, wherein the substituted alkyl or aryl has at least one substituent selected from hydrogen, halogen, hydroxy, amino, cyano, nitro, —S—($C_1$-$C_{10}$ alkyl), $C_1$-$C_{10}$ haloalkyl, $C_1$-$C_{10}$ alkyl, and $C_1$-$C_{10}$ alkoxy.

2. The method of claim 1, wherein the boron compound of the first step is selected from the group consisting of boric acid, trimethyl borate, triethyl borate, triisopropyl borate, tributyl borate, and triphenyl borate.

3. The method of claim 1, wherein the (R)- or (S)-binol of the first step is selected from the chemical structures represented by the following Chemical Formula 2:

[Chemical Formula 2]

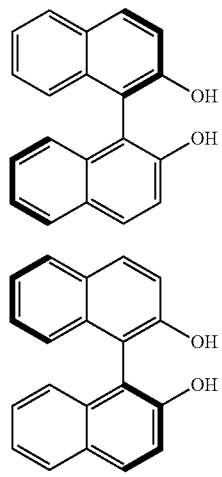

2-1

2-2

4. The method of claim 1, wherein the solvent in the first step is selected from the group consisting of acetonitrile, dichloromethane, toluene, and isopropanol.

5. The method of claim 1, wherein the boron compound and the (R)- or (S)-binol are added in an amount of 1 mole equivalent and 0.45-0.6 mole equivalents, respectively, based on 1 mole equivalent of the racemic compound represented by Chemical Formula 1 in the first step.

6. An amino alcohol-boron-binol complex represented by any of the following Chemical Formula 3:

[Chemical Formula 3]

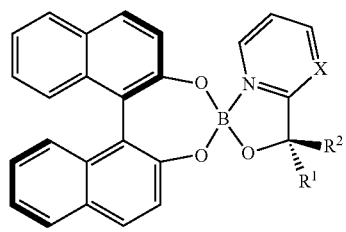

3-1-1

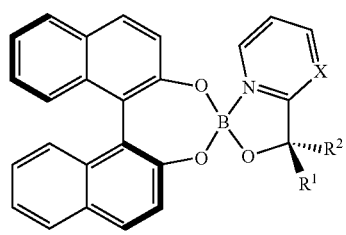

3-1-2

-continued

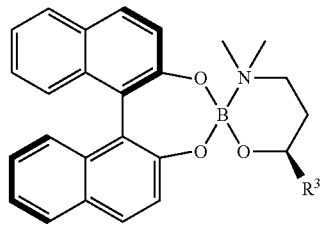

3-2-1

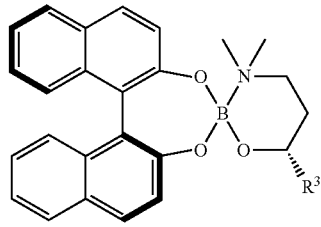

3-2-2

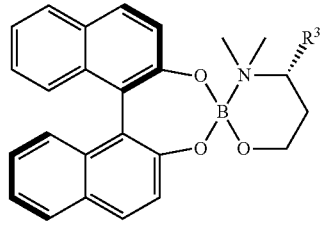

3-3-1

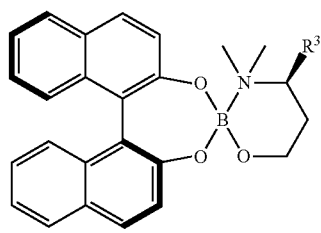

3-3-2

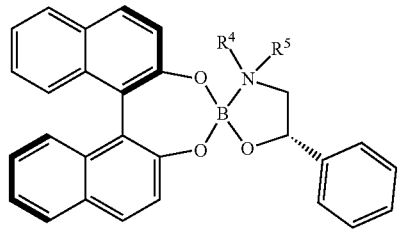

3-4-1

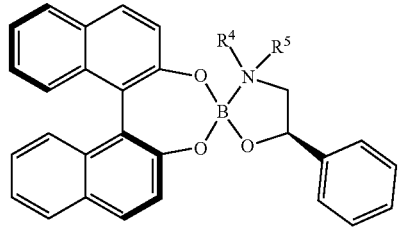

3-4-2

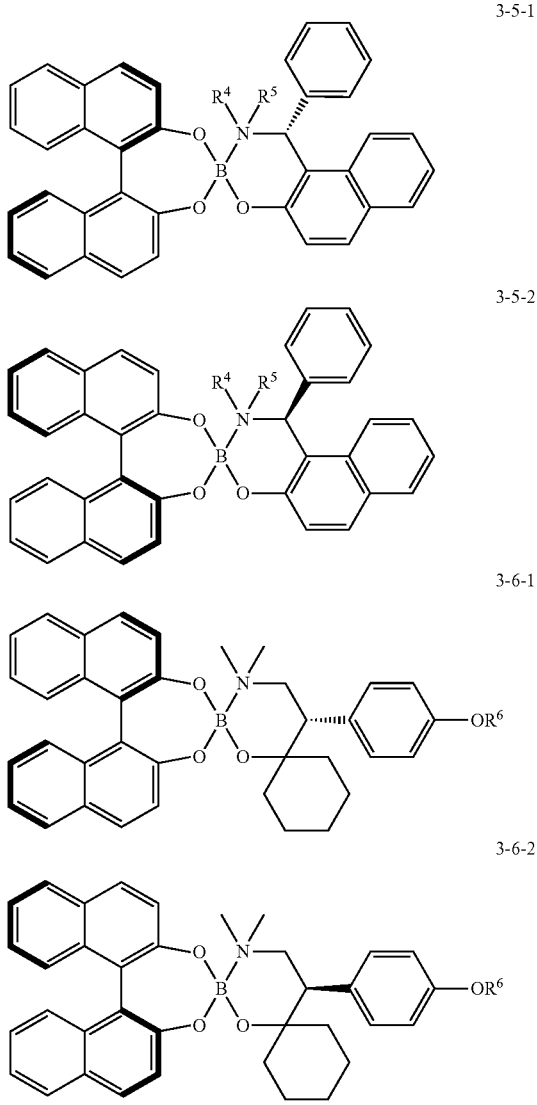

wherein,

X is CH, C—CH$_3$ or N;

R$^1$ is a hydrogen or a C$_1$-C$_{10}$ alkyl substituent;

R$^2$ is a substituent selected from the group consisting of a substituted or unsubstituted C$_1$-C$_{10}$ alkyl, a substituted or unsubstituted C$_2$-C$_{10}$ alkenyl, a substituted or unsubstituted C$_2$-C$_{10}$ alkynyl, a substituted or unsubstituted phenyl, a substituted or unsubstituted naphthyl, a substituted or unsubstituted pyrrolyl, a substituted or unsubstituted furanyl, a substituted or unsubstituted pyridinyl, a substituted or unsubstituted pyrimidinyl, and a substituted or unsubstituted pyranyl, wherein the substituted alkyl, alkenyl, alkynyl, phenyl, naphthyl, pyrrolyl, furanyl, pyridinyl, pyrimidinyl, or pyranyl has at least one substituent selected from the group consisting of hydrogen, halogen, hydroxy, amino, cyano, nitro, —S—(C$_1$-C$_{10}$ alkyl), C$_1$-C$_{10}$ haloalkyl, C$_1$-C$_{10}$ alkyl, benzyloxy, and C$_1$-C$_{10}$ alkoxy;

R$^3$ is a substituent selected from the group consisting of a substituted or unsubstituted phenyl, a substituted or unsubstituted thiophenyl, a substituted or unsubstituted pyrrolyl, a substituted or unsubstituted furanyl, a substituted or unsubstituted pyridinyl, a substituted or unsubstituted pyrimidinyl, and a substituted or unsubstituted pyranyl, wherein the substituted phenyl, thiophenyl, pyrrolyl, furanyl, pyridinyl, pyrimidinyl, or pyranyl has at least one substituent selected from the group consisting of hydrogen, halogen, hydroxy, amino, cyano, nitro, —S—(C$_1$-C$_{10}$ alkyl), C$_1$-C$_{10}$ haloalkyl, C$_1$-C$_{10}$ alkyl, and C$_1$-C$_{10}$ alkoxy;

R$^4$ and R$^5$ are each independently a substituted with a substituent selected from the group consisting of a substituted or unsubstituted C$_1$-C$_{10}$ alkyl, a substituted or unsubstituted pyrrolyl, a substituted or unsubstituted furanyl, a substituted or unsubstituted pyridinyl, a substituted or unsubstituted pyrimidinyl, and a substituted or unsubstituted pyranyl, wherein the substituted alkyl, pyrrolyl, furanyl, pyridinyl, pyrimidinyl, or pyranyl has at least one substituent selected from the group consisting of hydrogen, halogen, hydroxy, amino, cyano, nitro, —S—(C$_1$-C$_{10}$ alkyl), C$_1$-C$_{10}$ haloalkyl, C$_1$-C$_{10}$ alkyl, and C$_1$-C$_{10}$ alkoxy; or R$^4$ and R$^5$ form together a substituted or unsubstituted C$_4$-C$_{12}$ heterocycloalkyl, wherein the substituted heterocycloalkyl has at least one substituent selected from the group consisting of hydrogen, halogen, hydroxy, amino, cyano, nitro, —S—(C$_1$-C$_{10}$ alkyl), C$_1$-C$_{10}$ haloalkyl, C$_1$-C$_{10}$ alkyl, and C$_1$-C$_{10}$ alkoxy; and R$^6$ is a substituent selected from the group consisting of hydrogen, and a substituted or unsubstituted C$_1$-C$_{10}$ alkyl, wherein the substituted alkyl or aryl has at least one substituent selected from hydrogen, halogen, hydroxy, amino, cyano, nitro, —S—(C$_1$-C$_{10}$ alkyl), C$_1$-C$_{10}$ haloalkyl, C$_1$-C$_{10}$ alkyl, and C$_1$-C$_{10}$ alkoxy.

* * * * *